(12) United States Patent
Hwang et al.

(10) Patent No.: US 9,120,795 B2
(45) Date of Patent: Sep. 1, 2015

(54) CRYSTALLINE FORM OF A β-LACTAMASE INHIBITOR

(71) Applicant: Cubist Pharmaceuticals, Inc., Lexington, MA (US)

(72) Inventors: You Seok Hwang, Concord, MA (US); Jian-Qiao Gu, Lexington, MA (US); Akash Jain, Brulington, MA (US); Sudhakar Garad, Malden, MA (US); Jacob P. Sizemore, Shrewsbury, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 67 days.

(21) Appl. No.: 14/212,993

(22) Filed: Mar. 14, 2014

(65) Prior Publication Data

US 2014/0275001 A1    Sep. 18, 2014

Related U.S. Application Data

(60) Provisional application No. 61/784,143, filed on Mar. 14, 2013.

(51) Int. Cl.
*A61K 31/439* (2006.01)
*C07D 471/08* (2006.01)

(52) U.S. Cl.
CPC .................................. *C07D 471/08* (2013.01)

(58) Field of Classification Search
CPC ........................... A61K 31/439; C07D 471/08
See application file for complete search history.

(56) References Cited

U.S. PATENT DOCUMENTS

| | | | |
|---|---|---|---|
| 6,034,107 A | 3/2000 | Hirai et al. | |
| 6,194,442 B1 | 2/2001 | Hirai et al. | |
| 6,416,979 B1 | 7/2002 | Hirai et al. | |
| 6,953,807 B2 | 10/2005 | Hutin et al. | |
| 7,112,592 B2 | 9/2006 | Lampilas et al. | |
| 7,612,087 B2 | 11/2009 | Aszodi et al. | |
| 7,732,610 B2 | 6/2010 | Lampilas et al. | |
| 7,786,044 B2 | 8/2010 | Epp et al. | |
| 8,003,799 B2 | 8/2011 | Nieto-Roman et al. | |
| 8,178,554 B2 | 5/2012 | Lampilas et al. | |
| 8,268,753 B2 | 9/2012 | Epp et al. | |
| 8,288,553 B2 | 10/2012 | Priour et al. | |
| 8,471,025 B2 | 6/2013 | Dedhiya et al. | |
| 8,487,093 B2 | 7/2013 | Blizzard et al. | |
| 8,796,257 B2 | 8/2014 | Maiti et al. | |
| 2009/0227554 A1 | 9/2009 | Liversidge et al. | |
| 2010/0197928 A1 | 8/2010 | Priour et al. | |
| 2010/0286031 A1 | 11/2010 | Charan et al. | |
| 2011/0046102 A1 | 2/2011 | Ledoussal et al. | |
| 2011/0257079 A1 | 10/2011 | Chaudhary et al. | |
| 2012/0016553 A1 | 1/2012 | Bai | |
| 2012/0053350 A1 | 3/2012 | Mangion et al. | |
| 2012/0323010 A1 | 12/2012 | Ronsheim et al. | |
| 2013/0012712 A1 | 1/2013 | Priour et al. | |
| 2013/0059774 A1 | 3/2013 | Patel et al. | |
| 2013/0225554 A1 | 8/2013 | Maiti et al. | |
| 2013/0267480 A1 | 10/2013 | Dedhiya et al. | |
| 2013/0289012 A1 | 10/2013 | Gu et al. | |
| 2013/0296290 A1 | 11/2013 | Gu et al. | |
| 2013/0296291 A1 | 11/2013 | Gu et al. | |
| 2013/0296292 A1 | 11/2013 | Gu et al. | |
| 2013/0296293 A1 | 11/2013 | Gu et al. | |
| 2013/0296555 A1 | 11/2013 | Gu et al. | |
| 2013/0303504 A1 | 11/2013 | Gu et al. | |
| 2013/0345190 A1 | 12/2013 | Gu et al. | |

FOREIGN PATENT DOCUMENTS

| | | |
|---|---|---|
| EP | 2135959 A1 | 12/2012 |
| FR | 2 812 635 A1 | 2/2002 |
| FR | 2 835 186 A1 | 8/2003 |
| FR | 2 930 553 A1 | 10/2009 |
| FR | 2 951 171 A1 | 4/2011 |
| KR | 2010130176 A | 12/2010 |
| WO | 02010172 A1 | 7/2002 |
| WO | 03063864 A2 | 7/2003 |
| WO | 2005108391 A1 | 11/2005 |
| WO | 2006125974 A1 | 11/2006 |
| WO | 2007129176 A2 | 11/2007 |
| WO | 2009091856 A2 | 7/2009 |
| WO | 2009133442 A1 | 11/2009 |
| WO | 2010118361 A1 | 1/2010 |
| WO | 2010056827 A1 | 5/2010 |
| WO | 2010126820 A1 | 11/2010 |
| WO | 2011042560 A1 | 4/2011 |
| WO | 2011101710 A1 | 8/2011 |
| WO | 2012086241 A1 | 6/2012 |
| WO | 2012172368 A1 | 12/2012 |
| WO | 2013014496 A1 | 1/2013 |
| WO | 2013014497 A1 | 1/2013 |
| WO | 2013030735 A1 | 3/2013 |
| WO | 2013038330 A1 | 3/2013 |
| WO | WO 2013030735 A1 * | 3/2013 |
| WO | 2013149121 A1 | 10/2013 |
| WO | 2013180197 A1 | 12/2013 |

OTHER PUBLICATIONS

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture-activity relationships in the S-3578 series"; Bioorganic and Medicinal Chemistry 2004, vol. 12, pp. 4211-4219.

(Continued)

*Primary Examiner* — Andrew D Kosar
*Assistant Examiner* — John S Kenyon
(74) *Attorney, Agent, or Firm* — Lathrop & Gage LLP; Brian C. Trinque; David F. Cauble

(57) ABSTRACT

This disclosure provides compositions containing solid forms of sodium (2S,5R)-2-(1,3,4-oxadiazol-2-yl)-7-oxo-1,6-diazabicyclo[3.2.1]octan-6-yl sulfate, and methods of manufacturing and using these compositions.

20 Claims, 7 Drawing Sheets

(56) References Cited

OTHER PUBLICATIONS

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-yl)-2-ethoxyiminoacetamido] cephalosporins bearing 4-[3-(aminoalkyl)-ureido]-1-pyridinium at C-3'"; Bioorganic and Medicinal Chemistry 2004, vol. 12, pp. 4221-4231.

Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure-activity Relationships"; The Journal of Antibiotics 2002, vol. 55, No. 11, pp. 975-992.

Ida, T. et al. "CP6679, a new injectable cephalosporin with broad spectrum and potent activities against methicillin- resistant *Staphylococcus aureus* and *Pseudomonas aeruginosa*"; Journal of Infection and Chemotherapy 2002, vol. 8, pp. 138-144.

Blizzard et al: Side chain SAR of bicyclic beta-lactamase inhibitors (Blls). 1. discovery of a class C BLI for combination with imipinem; Bioorganic & Medicinal Chemistry Letters; 2010, vol. 20, pp. 918-921.

Coleman: Diazabicyclooctanes (DBOs): a potent new class of non-beta-lactam beta-lactamase inhibitors; Current Opinion in Microbiology; 2011, vol. 14, pp. 1-6.

Miller et al: Practical and Cost-Effective Manufacturing Route for the Synthesis of a beta-Lactamase Inhibitor; Organic Letters, 2014, vol. 16, No. 1, pp. 174-177.

Crompton, et al: Beta-Lactamase inhibitors, the inhibition of serine beta-lactamases by specific boronic acids; Biochem J., 1988, vol. 251, pp. 453-459.

International Search Report and Written Opinion for International Application No. PCT/US2013/034562, dated Jul. 30, 2013, 11 pages.

Mangion, et al: A Concise of a beta-Lactamase Inhibitor; Organic Letters, Oct. 21, 2011, 13(2), pp. 5480-5483.

Patani, et al: Bioisosterism: A Rational Approach in Drug Design; Chern Rev, 1996, vol. 96, pp. 3147-3176.

International Search Report and Written Opinion for International Application No. PCT/US2013/034589, dated Jul. 29, 2013, 11 pages.

Non-Final Office Action issued for U.S. Appl. No. 14/214,234, mailed Jul. 7, 2014 (16 pages).

\* cited by examiner 1. 1, 2-Dimethoxyethane at 50°C for 3 days
2. DCM at 50°C for 24 hours
3. IPA/water (98:2) at 50°C for 3 days
4. Ambient conditions
5. IPA/water (98:2) cycling 25- 50°C for 3 days
6. Storage at 25°C and 96% RH
7. IPA/water (98:2) at 50°C for 3 days
8. Storage at 25° C and RH > 80%
9. Storage at 25° C and RH < 60%
10. Storage at 60° C for 24 hours
11. Storage at 40° C and 75% RH

CRYSTALLINE FORM OF A β-LACTAMASE INHIBITOR

CROSS-REFERENCE TO RELATED APPLICATIONS

This application claims priority to U.S. Provisional Application No. 61/784,143, filed Mar. 14, 2013, the content of which is incorporated herein by reference in its entirety.

TECHNICAL FIELD

This disclosure relates to solid forms of sodium (2S,5R)-2-(1,3,4-oxadiazol-2-yl)-7-oxo-1,6-diazabicyclo[3.2.1]octan-6-yl sulfate, and related compositions and methods.

BACKGROUND

The crystal state of a compound can be important when the compound is used for pharmaceutical purposes. Compared with an amorphous solid, the solid physical properties of a crystalline compound can change, which can affect its suitability for pharmaceutical use. For example, a particular crystalline compound can overcome the disadvantage of other solid forms of the compound that readily absorb moisture (high hygroscopicity). For an ionic drug substance, high hygroscopicity can diminish the drug product's stability profile by a host of mechanisms, as the drug substance may have a propensity to absorb water. Water that is absorbed from the environment (packaging materials, exposure to air, or in the case of formulated products, from other materials), can lead to degradation products and/or impurities in a drug product or add to the cost of manufacturing the drug product with acceptably low levels of water.

There is a need for solid forms of (2S,5R)-2-(1,3,4-oxadiazol-2-yl)-7-oxo-1,6-diazabicyclo[3.2.1]octan-6-yl hydrogen sulfate for use in drug substance and drug product development.

SUMMARY

Solid forms of sodium (2S,5R)-2-(1,3,4-oxadiazol-2-yl)-7-oxo-1,6-diazabicyclo[3.2.1]octan-6-yl sulfate, and compositions comprising these solid forms, are provided herein, in addition to various methods of preparing these compositions. A crystalline sodium (2S,5R)-2-(1,3,4-oxadiazol-2-yl)-7-oxo-1,6-diazabicyclo[3.2.1]octan-6-yl sulfate solid form provided herein has advantageous characteristics that are beneficial to the preparation of various drug formulations. For example, the hydrate form of sodium (2S,5R)-2-(1,3,4-oxadiazol-2-yl)-7-oxo-1,6-diazabicyclo[3.2.1]octan-6-yl sulfate is less hygroscopic compared to the amorphous form of this compound. These solid forms can have good stability in the process of preparation, packing, transportation, and storage.

Sodium (2S,5R)-2-(1,3,4-oxadiazol-2-yl)-7-oxo-1,6-diazabicyclo[3.2.1]octan-6-yl sulfate, and solvates thereof, can be obtained in various solid forms. In one aspect, provided herein is a particularly preferred crystalline sodium (2S,5R)-2-(1,3,4-oxadiazol-2-yl)-7-oxo-1,6-diazabicyclo[3.2.1]octan-6-yl sulfate solid designated herein as "Hydrate 1". Hydrate 1 is a trihydrate, and has the following structure:

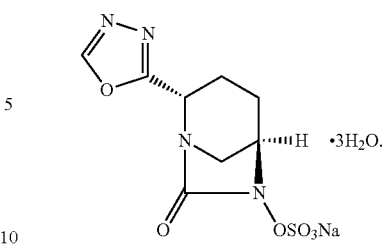

In an embodiment, Hydrate 1 is characterized by an X-ray powder diffraction pattern having peaks expressed in degrees 2-Theta at angles of 13.09±0.3°, 13.79±0.3°, 14.29±0.3°, 20.49±0.3°, 21.46±0.3°, 22.21±0.3°, 26.10±0.3°, 26.87±0.3°, 28.65±0.3°, and 33.46±0.3°. Hydrate 1 can also be characterized by an X-ray powder diffraction pattern having peaks expressed in degrees 2-Theta at angles of 13.09±0.3°, 14.29±0.3°, 20.49±0.3°, 21.46±0.3°, and 22.21±0.3°.

The crystalline Hydrate 1 can be further characterized by a differential scanning calorimetry (DSC) thermogram having three main events; a dehydration (40° C.-165° C.) and two degradation/decomposition steps (onset at ~160° C. and 240° C., respectively). In another embodiment, Hydrate 1 is further characterized by a thermogravimetry (TGA) curve. Three distinct events observed by DSC are associated with weight losses by TGA. The endothermic first event occurs between 40° C.-165° C., with a corresponding loss of 13.1% w/w loss on the TGA is attribute to loss of water of hydration. The other two events, an exothermic second event (165° C.-240° C.; 12.1% w/w) and an endothermic third event (240° C.-330° C.; 18.8% w/w) can be attributable to sample degradation or decomposition (FIG. 3).

Also provided are pharmaceutical compositions comprising Hydrate 1 and a pharmaceutically acceptable carrier.

In another aspect, provided herein is a method for the treatment of bacterial infections in a subject, comprising administering to said mammal a therapeutically effective amount of Hydrate 1. In an embodiment of this method, Hydrate 1 can be characterized by an X-ray powder diffraction pattern having peaks expressed in degrees 2-Theta at angles of 13.1±0.3°, 13.8±0.3°, 14.3±0.3°, 20.5±0.3°, 21.5±0.3°, 22.2±0.3°, 26.1±0.3°, 26.9±0.3°, 28.7±0.3°, and 33.5±0.3°. In another embodiment, Hydrate 1 can also be characterized by an X-ray powder diffraction pattern having peaks expressed in degrees 2-Theta at angles of 13.1±0.3°, 14.3±0.3°, 20.5±0.3°, 21.5±0.3°, and 22.2±0.3°.

DETAILED DESCRIPTION

Figure 1:
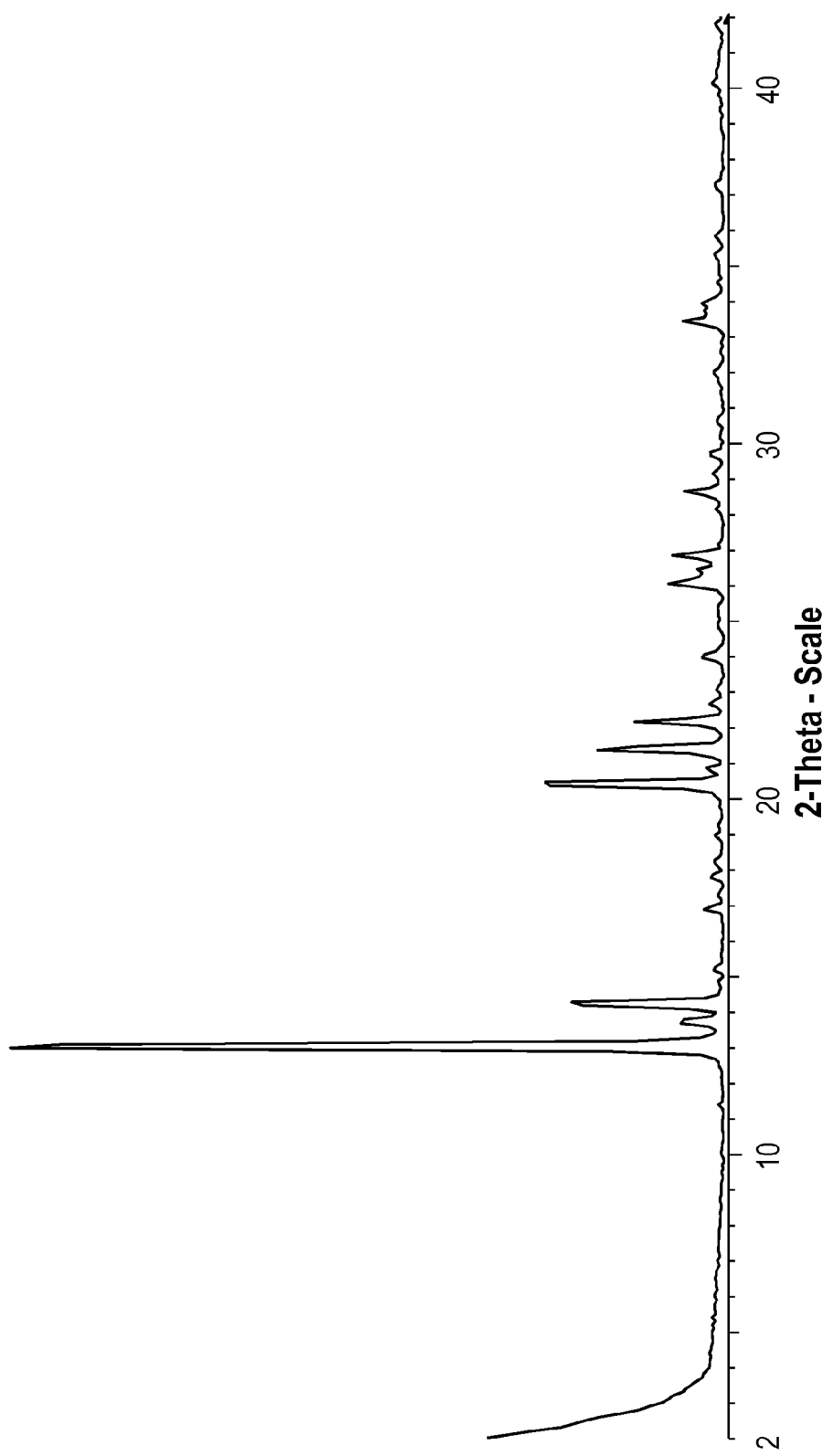
FIG. 1 depicts the X-ray powder diffraction pattern of Hydrate 1 of sodium (2S,5R)-2-(1,3,4-oxadiazol-2-yl)-7-oxo-1,6-diazabicyclo[3.2.1]octan-6-yl sulfate.

Bacterial resistance to β-lactam antibiotics, especially in Gram-negative bacteria, is most commonly mediated by β-lactamases. β-lactamases are enzymes that catalyze the hydrolysis of the β-lactam ring, which inactivates the antibacterial activity of the β-lactam antibiotic and allows the bacteria to become resistant. Inhibition of the β-lactamase with a β-lactamase inhibitor (BLI) slows or prevents degradation of the β-lactam antibiotic and restores β-lactam antibiotic susceptibility to β-lactamase producing bacteria. Sodium (2S,5R)-2-(1,3,4-oxadiazol-2-yl)-7-oxo-1,6-diazabicyclo[3.2.1]octan-6-yl sulfate is an effective BLI.

Sodium (2S,5R)-2-(1,3,4-oxadiazol-2-yl)-7-oxo-1,6-diazabicyclo[3.2.1]octan-6-yl sulfate can occur in an amorphous solid form or in a crystalline solid form. Crystalline solid forms of sodium (2S,5R)-2-(1,3,4-oxadiazol-2-yl)-7-oxo-1,6-diazabicyclo[3.2.1]octan-6-yl sulfate can exist in one or more unique polymorph forms, which may additionally comprise one or more equivalents of water (i.e., a hydrate of sodium (2S,5R)-2-(1,3,4-oxadiazol-2-yl)-7-oxo-1,6-diazabicyclo[3.2.1]octan-6-yl sulfate).

Sodium (2S,5R)-2-(1,3,4-oxadiazol-2-yl)-7-oxo-1,6-diazabicyclo[3.2.1]octan-6-yl sulfate as represented by the structure below.

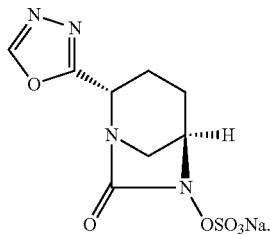

Accordingly, provided herein are hydrates of crystalline sodium (2S,5R)-2-(1,3,4-oxadiazol-2-yl)-7-oxo-1,6-diazabicyclo[3.2.1]octan-6-yl sulfate. In particular, provided herein is "Hydrate 1", a particular hydrate of crystalline sodium (2S,5R)-2-(1,3,4-oxadiazol-2-yl)-7-oxo-1,6-diazabicyclo[3.2.1]octan-6-yl sulfate.

Polymorphism

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, stability, solubility, dissolution rate, etc., which can, in turn, affect the stability, dissolution rate and/or bioavailability of a given polymorph and its suitability for use as a pharmaceutical and in pharmaceutical compositions.

Access to different polymorphs of sodium (2S,5R)-2-(1,3,4-oxadiazol-2-yl)-7-oxo-1,6-diazabicyclo[3.2.1]octan-6-yl sulfate is desirable for other reasons as well. One such reason is that different polymorphs of a compound (e.g., sodium (2S,5R)-2-(1,3,4-oxadiazol-2-yl)-7-oxo-1,6-diazabicyclo[3.2.1]octan-6-yl sulfate) can incorporate different impurities, or chemical residues, upon crystallization. Certain polymorphs incorporate very little, or no, chemical residues. Accordingly, the formation of certain polymorph forms of a compound may result in purification of the compound.

Crystalline Hydrate 1 exhibits low hygroscopicity relative to amorphous sodium (2S,5R)-2-(1,3,4-oxadiazol-2-yl)-7-oxo-1,6-diazabicyclo[3.2.1]octan-6-yl. Low hygroscopicity of a solid compound is desirable for several reasons. For example, compounds that are highly hygroscopic may be chemically unstable, or unsuitable for formulating as a drug product due to changes of the drug form's physical characteristics (e.g., bulk density, dissolution rate, etc.) that can occur if it is stored in settings with varying relative humidity. Also, hygroscopicity can impact large-scale manufacturing and handling of a compound. For example, it can be difficult to determine the true weight of a hygroscopic active agent when preparing a pharmaceutical composition comprising that agent.

Figure 4:
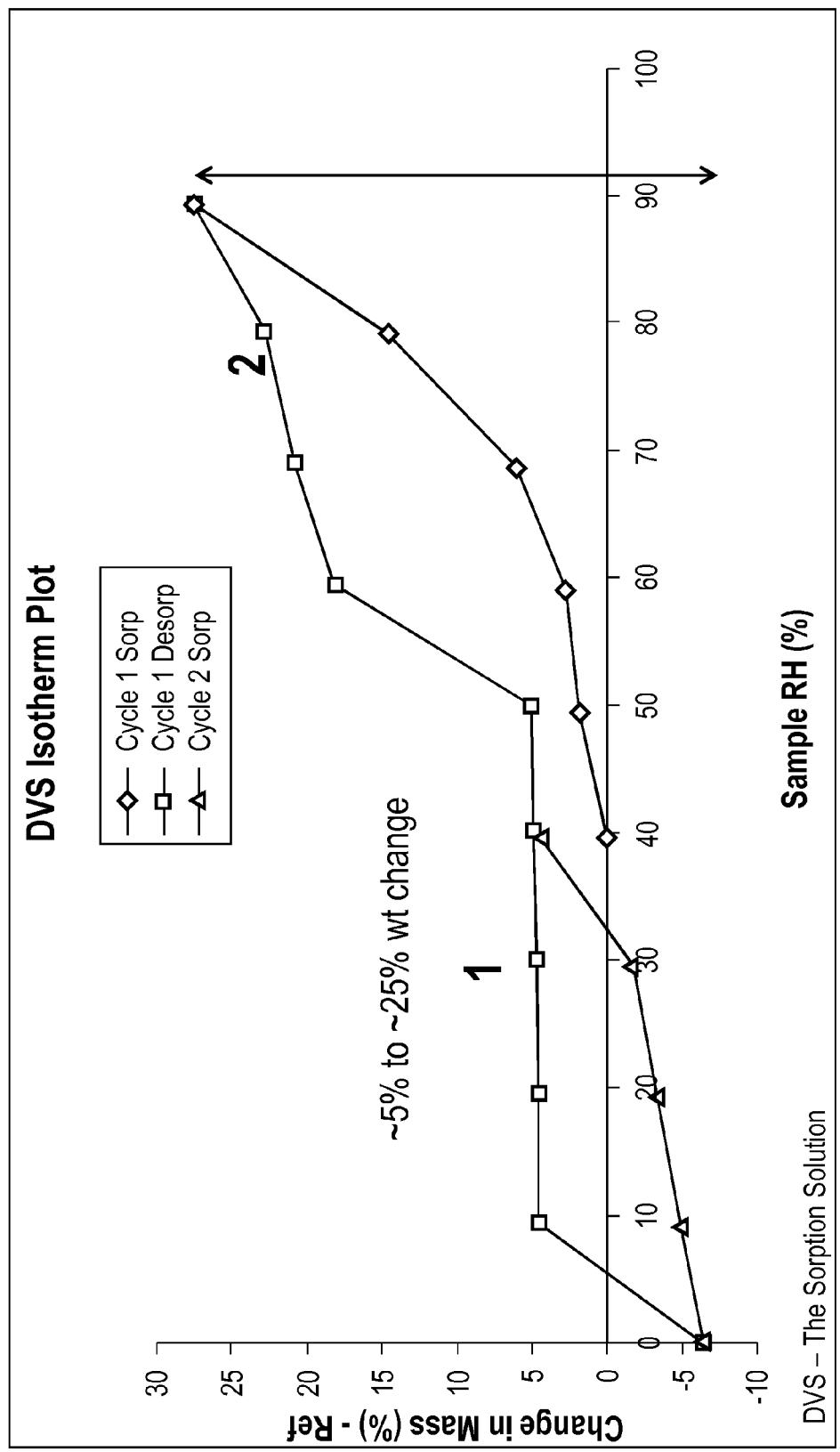
FIG. 4 depicts the DVS graph of amorphous sodium (2S,5R)-2-(1,3,4-oxadiazol-2-yl)-7-oxo-1,6-diazabicyclo[3.2.1]octan-6-yl sulfate.
Figure 5:
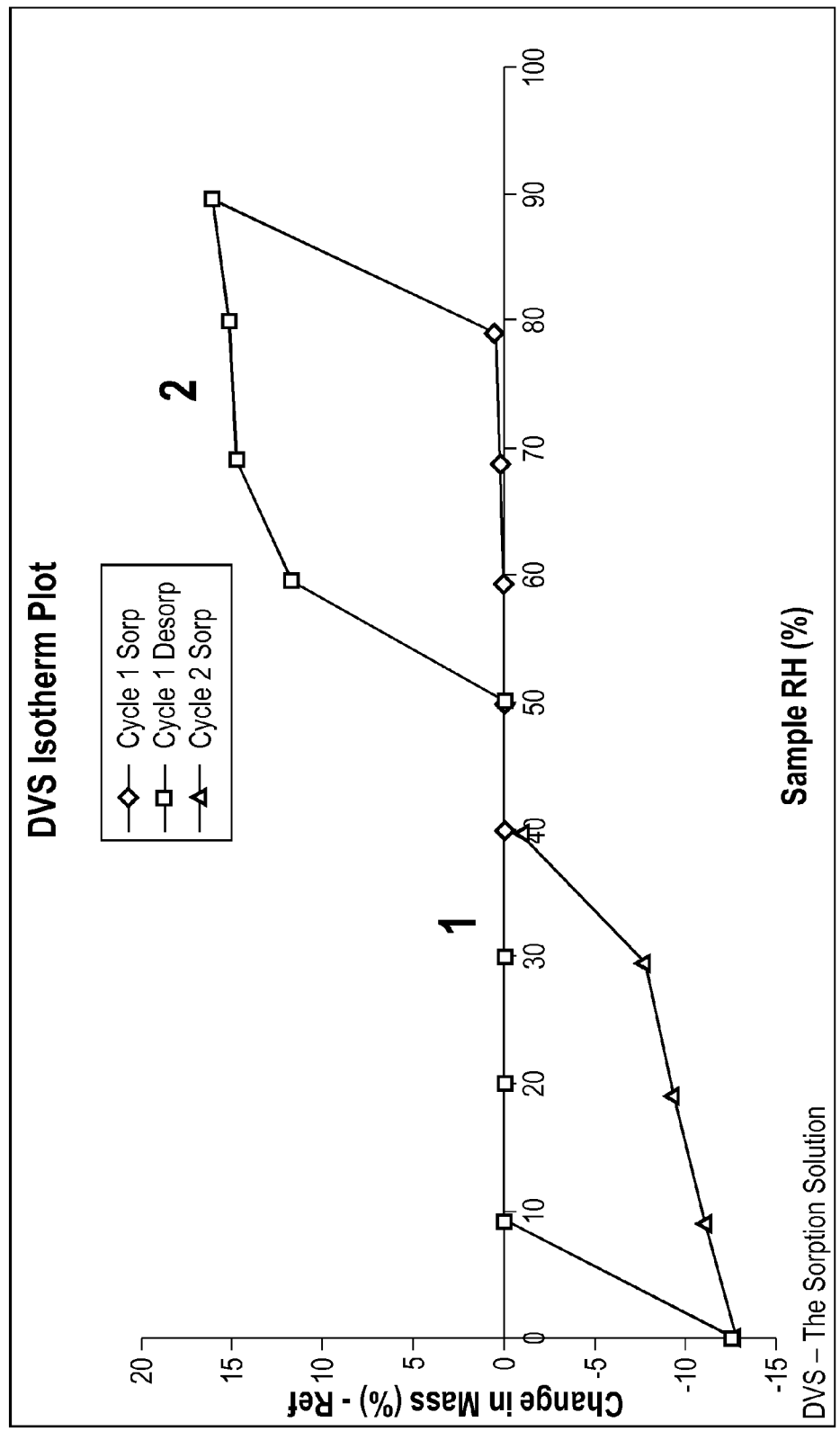
FIG. 5 depicts the DVS graph of Hydrate 1.

FIG. 4 depicts the DVS graph of amorphous sodium (2S,5R)-2-(1,3,4-oxadiazol-2-yl)-7-oxo-1,6-diazabicyclo[3.2.1]octan-6-yl sulfate. In contrast, FIG. 5 depicts the DVS graph of Hydrate 1. As can be seen, Hydrate 1 is significantly less hygroscopic than the amorphous form of this compound.

Figure 2:
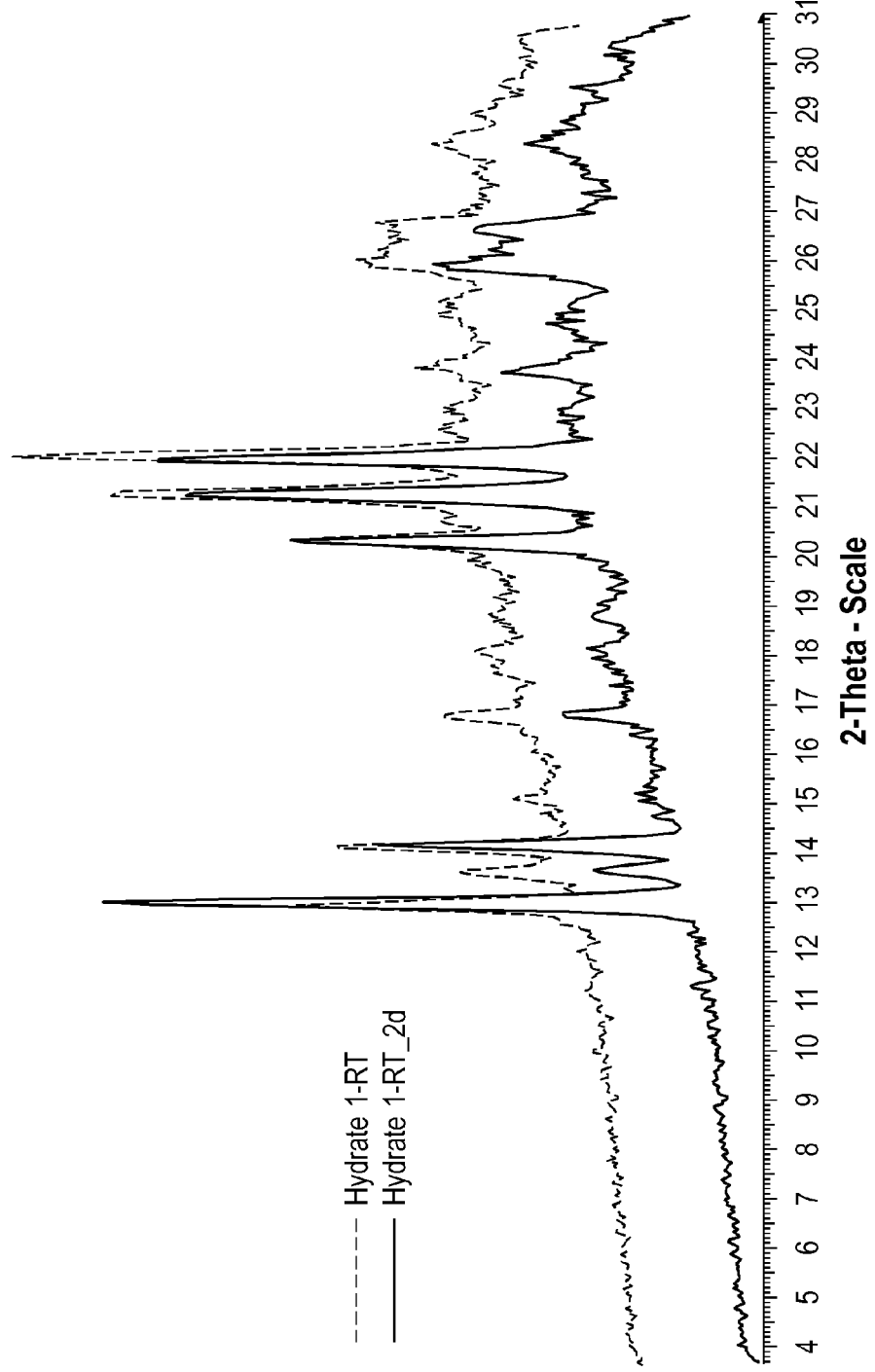
FIG. 2 depicts the thermal stability of Hydrate 1 at 25° C. at 40% relative humidity over 2 days.

The Hydrate 1 has also demonstrated favorable stability. For example, FIG. 2 depicts the thermal stability of Hydrate 1 at 25° C. at 40% relative humidity over 2 days. As shown in this figure, there is little to no change to the Hydrate 1 crystal form over this time period.

Characterization of Polymorphs

In certain embodiments, the compounds of the invention are identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials.

One embodiment of crystalline sodium (2S,5R)-2-(1,3,4-oxadiazol-2-yl)-7-oxo-1,6-diazabicyclo[3.2.1]octan-6-yl sulfate is referred to herein as Hydrate 1. In one embodiment, Hydrate 1 is characterized by an X-ray powder diffraction pattern having one or more characteristic peaks expressed in degrees 2-Theta at angles selected from 13.1±0.3°, 14.3±0.3°, 20.5±0.3°, 21.5±0.3°, and 22.2±0.3°. In another embodiment, Hydrate 1 is characterized by an X-ray powder diffraction pattern having one or more peaks expressed in degrees 2-Theta at angles selected from 13.1±0.3°, 14.3±0.3°, 20.5±0.3°, and 21.5±0.3°. In another embodiment, Hydrate 1 is characterized by an X-ray powder diffraction pattern having one or more peaks expressed in degrees 2-Theta at angles selected from 13.1±0.3°, 14.3±0.3°, 20.5±0.3°, 21.5±0.3°, and 22.2±0.3°. In another embodiment, Hydrate 1 is characterized by an X-ray powder diffraction pattern having one or more peaks expressed in degrees 2-Theta at angles selected from 13.1±0.3°, 13.8±0.3°, 14.3±0.3°, 20.5±0.3°, 21.5±0.3°, 22.2±0.3°, 26.1±0.3°, 26.8±0.3°, 28.7±0.3°, and 33.5±0.3°.

In another embodiment, Hydrate 1 is characterized by an X-ray powder diffraction pattern having one or more characteristic peaks expressed in degrees 2-Theta at angles selected from 13.1±0.2°, 14.3±0.2°, 20.5±0.2°, 21.5±0.2°, and 22.2±0.2°. In another embodiment, Hydrate 1 is characterized by an X-ray powder diffraction pattern having one or more peaks expressed in degrees 2-Theta at angles selected from 13.1±0.2°, 14.3±0.2°, 20.5±0.2°, and 21.5±0.2°. In another embodiment, Hydrate 1 is characterized by an X-ray powder diffraction pattern having one or more peaks expressed in degrees 2-Theta at angles selected from 13.1±0.2°, 14.3±0.2°, 20.5±0.2°, 21.5±0.2°, and 22.2±0.2°. In another embodiment, Hydrate 1 is characterized by an X-ray powder diffraction pattern having one or more peaks expressed in degrees 2-Theta at angles selected from 13.1±0.2°, 13.8±0.2°, 14.3±0.2°, 20.5±0.2°, 21.5±0.2°, 22.2±0.2°, 26.1±0.2°, 26.9±0.2°, 28.7±0.2°, and 33.5±0.2°.

In another embodiment, Hydrate 1 is characterized by an X-ray powder diffraction pattern having one or more characteristic peaks expressed in degrees 2-Theta at angles selected from 13.1, 14.3, 20.5, 21.5, and 22.2. In another embodiment, Hydrate 1 is characterized by an X-ray powder diffraction pattern having one or more peaks expressed in degrees 2-Theta at angles selected from 13.1, 14.3, 20.5, and 21.5. In another embodiment, Hydrate 1 is characterized by an X-ray powder diffraction pattern having one or more peaks expressed in degrees 2-Theta at angles selected from 13.1, 14.3, 20.5, 21.5, and 22.2. In another embodiment, Hydrate 1 is characterized by an X-ray powder diffraction pattern having one or more peaks expressed in degrees 2-Theta at angles selected from 13.1, 13.8, 14.3, 20.5, 21.5, 22.2, 26.1, 26.9, 28.7, and 33.5.

In one embodiment, Hydrate 1 is characterized by an X-ray powder diffraction pattern having peaks substantially in accordance with FIG. 1. In another embodiment, Hydrate 1 is characterized by an X-ray powder diffraction pattern having peaks substantially in accordance with Table 6.

Figure 3:
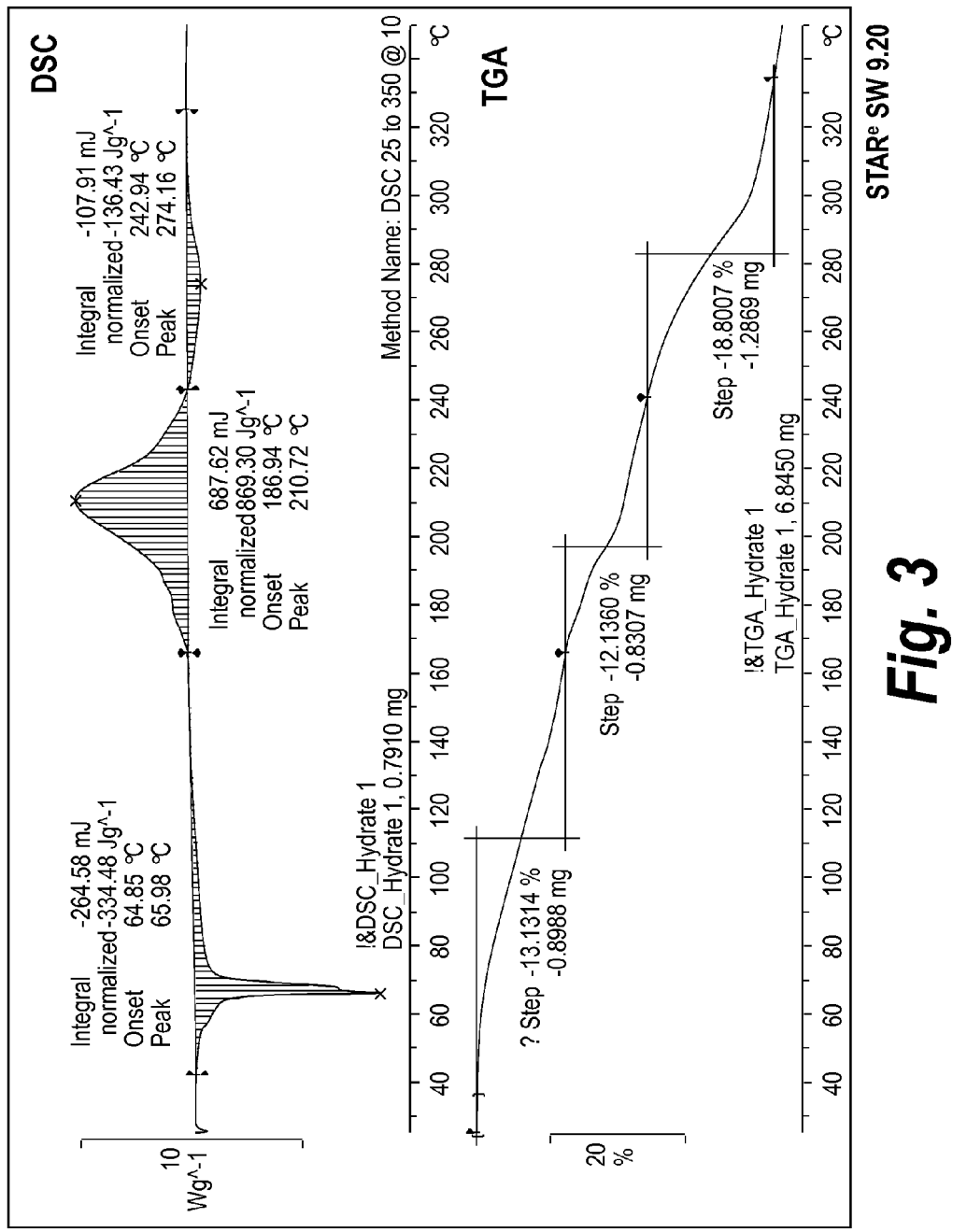
FIG. 3 depicts the differential scanning calorimetry (DSC) thermogram and the thermogravimetry curve of Hydrate 1.

The crystalline Hydrate 1 can be further characterized by a differential scanning calorimetry (DSC) thermogram having three main events; a dehydration (40° C.-165° C.) and two degradation/decomposition steps (onset at ~160° C. and 240° C., respectively). In another embodiment, Hydrate 1 is further characterized by a thermogravimetry (TGA) curve. Three distinct events observed by DSC are associated with weight losses by TGA. The endothermic first event occurs between 40° C.-165° C., with a corresponding loss of 13.1% w/w loss on the TGA is attribute to loss of water of hydration. The other two events, an exothermic second event (165° C.-240° C.; 12.1% w/w) and an endothermic third event (240° C.-330° C.; 18.8% w/w) can be attributable to sample degradation or decomposition (FIG. 3).

In certain embodiments, Hydrate 1 may contain impurities. Non-limiting examples of impurities include undesired polymorph forms, or residual organic and inorganic molecules such as solvents, water or salts.

In another embodiment, Hydrate 1 is substantially free from impurities. In another embodiment, Hydrate 1 contains less than 10% by weight total impurities. In another embodiment, Hydrate 1 contains less than 5% by weight total impurities. In another embodiment, Hydrate 1 contains less than 1% by weight total impurities. In yet another embodiment, Hydrate 1 contains less than 0.1% by weight total impurities.

In certain embodiments, Hydrate 1 is a crystalline solid substantially free of amorphous sodium (2S,5R)-2-(1,3,4-oxadiazol-2-yl)-7-oxo-1,6-diazabicyclo[3.2.1]octan-6-yl sulfate. As used herein, the term "substantially free of amorphous sodium (2S,5R)-2-(1,3,4-oxadiazol-2-yl)-7-oxo-1,6-diazabicyclo[3.2.1]octan-6-yl sulfate" means that the compound contains no significant amount of amorphous sodium (2S,5R)-2-(1,3,4-oxadiazol-2-yl)-7-oxo-1,6-diazabicyclo[3.2.1]octan-6-yl sulfate. In certain embodiments, at least about 95% by weight of crystalline Hydrate 1 is present. In still other embodiments of the invention, at least about 99% by weight of crystalline Hydrate 1 is present.

In another embodiment, Hydrate 1 is substantially free of Hydrates 2, 3, 4, 5, 6, or 7. As used herein, the term "substantially free of Hydrates 2, 3, 4, 5, 6, or 7" means that Hydrate 1 contains no significant amount of Hydrates 2, 3, 4, 5, 6, or 7. In certain embodiments, at least about 95% by weight of crystalline Hydrate 1 is present. In still other embodiments of the invention, at least about 99% by weight of crystalline Hydrate 1 is present.

Processes and Methods

Provided herein is a method of making crystalline sodium (2S,5R)-2-(1,3,4-oxadiazol-2-yl)-7-oxo-1,6-diazabicyclo[3.2.1]octan-6-yl sulfate, comprising:

(1) combining sodium (2S,5R)-2-(1,3,4-oxadiazol-2-yl)-7-oxo-1,6-diazabicyclo[3.2.1]octan-6-yl sulfate and a solvent, such that a solution of sodium (2S,5R)-2-(1,3,4-oxadiazol-2-yl)-7-oxo-1,6-diazabicyclo[3.2.1]octan-6-yl sulfate is formed; and (2) evaporating the solvent, such that crystalline sodium (2S,5R)-2-(1,3,4-oxadiazol-2-yl)-7-oxo-1,6-diazabicyclo[3.2.1]octan-6-yl sulfate is formed.

In another embodiment, provided herein is a method of making Hydrate 1, comprising:

(1) combining sodium (2S,5R)-2-(1,3,4-oxadiazol-2-yl)-7-oxo-1,6-diazabicyclo[3.2.1]octan-6-yl sulfate and a solvent, such that a solution of sodium (2S,5R)-2-(1,3,4-oxadiazol-2-yl)-7-oxo-1,6-diazabicyclo[3.2.1]octan-6-yl sulfate is formed; and (2) evaporating the solvent, such that Hydrate 1 is formed.

In certain embodiments of these methods, the solvent is anisole, ethyl acetate, isopropyl acetate, methylisobutyl ketone, 2-propanol, dimethyl sulfoxide, t-butylmethyl ether, toluene, tetrahydrofuran, dichloromethane, acetonitrile, nitromethane, isopropyl alcohol, water, or mixtures thereof.

In step (1) of these methods, the sodium (2S,5R)-2-(1,3,4-oxadiazol-2-yl)-7-oxo-1,6-diazabicyclo[3.2.1]octan-6-yl sulfate can be in an amorphous form. In one embodiment, an amorphous form of the compound is formed by combining sodium (2S,5R)-2-(1,3,4-oxadiazol-2-yl)-7-oxo-1,6-diazabicyclo[3.2.1]octan-6-yl sulfate with a solvent, such as water, followed by freeze drying or lyophilization.

In certain embodiments, any one of the above methods is a method of making Hydrate 1 wherein the method further comprises: (3) drying the crystalline compound to form Hydrate 1.

Also provided herein is a method of making Hydrate 1 comprising:

(1) combining sodium (2S,5R)-2-(1,3,4-oxadiazol-2-yl)-7-oxo-1,6-diazabicyclo[3.2.1]octan-6-yl sulfate and a solvent, such that a solution of sodium (2S,5R)-2-(1,3,4-oxadiazol-2-yl)-7-oxo-1,6-diazabicyclo[3.2.1]octan-6-yl sulfate is formed; and (2) combining an antisolvent with the solution, wherein the antisolvent is miscible with the solvent and wherein sodium (2S,5R)-2-(1,3,4-oxadiazol-2-yl)-7-oxo-1,6-diazabicyclo[3.2.1]octan-6-yl sulfate is partially or completely insoluble in the antisolvent, such that crystalline Hydrate 1 precipitates from the solution.

In certain embodiments of this solvent/antisolvent method, the solvent is water, and the antisolvent is THF or acetonitrile.

Pharmaceutical Compositions Comprising Hydrate 1 and Use Thereof

Provided herein are pharmaceutical compositions or formulations comprising Hydrate 1. Also provided herein are pharmaceutical compositions or formulations comprising Hydrate 1 further comprising a β-lactam antibiotic.

The pharmaceutical compositions can be formulated for oral, intravenous, intramuscular, subcutaneous or parenteral administration for the therapeutic or prophylactic treatment of diseases, such as bacterial infections. Preferably, the pharmaceutical composition is formulated for intravenous administration.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein, preferably Hydrate 1 in conjunction with a β-lactam antibiotic, in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Non-limiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention preferably in conjunction with a β-lactam antibiotic, can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, fillers, lubricants, disintegrants, or acceptable wetting agents. Oral liquid preparations generally are in the form of aqueous or oily solutions, suspensions, emulsions, syrups or elixirs.

For intravenous (IV) use, the pharmaceutical composition, preferably Hydrate 1 in conjunction with a β-lactam antibiotic, can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Pharmaceutical compositions of this invention for parenteral injection comprise pharmaceutically-acceptable aqueous or non-aqueous solutions, dispersions, suspensions or emulsions as well as sterile powders for reconstitution into sterile injectable solutions or dispersions just prior to use.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

For intramuscular preparations, a sterile formulation of compounds, preferably Hydrate 1 in conjunction with a β-lactam antibiotic, or suitable soluble salt forms thereof, for example hydrochloride salts, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds, preferably Hydrate 1 in conjunction with a β-lactam antibiotic, may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions, preferably Hydrate 1 in conjunction with a β-lactam antibiotic, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal administration, the pharmaceutical compositions, preferably Hydrate 1 in conjunction with a β-lactam antibiotic, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably Hydrate 1 in conjunction with a β-lactam antibiotic, can be a solution of one or more compounds, or salts thereof, in a suitable diluent, in sterile hermetically sealed ampoules or sterile syringes. The concentration of the compounds, preferably Hydrate 1 in conjunction with a β-lactam antibiotic, in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention, preferably in combination with a β-lactam antibiotic for the drugs in the art-recognized protocols.

As used herein, the phrases "therapeutically-effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies. The term "treating" or "treatment" is defined as administering, to a subject, a therapeutically-effective amount of one or more compounds both to prevent the occurrence of an infection and to control or eliminate an infection. Those in need of treatment may include individuals already having a particular medical disease as well as those at risk for the disease (i.e., those who are likely to ultimately acquire the disorder). The term "subject," as used herein, refers to a mammal, a plant, a lower animal, or a cell culture. In one embodiment, a subject is a human or other animal patient in need of antibacterial treatment.

The term "administering" or "administration" and the like, refers to providing the Hydrate 1 to the subject in need of treatment. Preferably the subject is a mammal, more preferably a human. The present invention comprises administering Hydrate 1 in conjunction with a β-lactam antiobiotic. When Hydrate 1 is administered in conjunction with a β-lactam antiobiotic, Hydrate 1 and the β-lactam antiobiotic can be administered at the same time or different times. When Hydrate 1 and the β-lactam antiobiotic are administered at the same time, they can be administered as a single composition or pharmaceutical composition or they can be administered separately. It is understood that when Hydrate 1 is administered in conjunction with a β-lactam antiobiotic, that the active agents can be administered in a single combination or in multiple combinations. For example, when administered by IV, Hydrate 1 can be dissolved or suspended in any of the commonly used intravenous fluids and administered by infusion, then a β-lactam antibiotic can be dissolved or suspended in any of the commonly used intravenous fluids and administered by infusion. Conversely the β-lactam antibiotic can be dissolved or suspended in any of the commonly used intravenous fluids and administered by infusion, then Hydrate 1 can be dissolved or suspended in any of the commonly used intravenous fluids and administered by infusion. Alternatively, a pharmaceutical composition comprising Hydrate 1 and a β-lactam antibiotic can be dissolved or suspended in any of the commonly used intravenous fluids and administered by infusion.

In one embodiment of the invention, is provided a method of treating or preventing a bacterial infection comprising administering to a subject in need thereof a therapeutically-effective amount of the pharmaceutical composition comprising Hydrate 1 and a β-lactam antibiotic.

In one embodiment of the invention, is provided a method of treating or preventing a bacterial infection comprising administering to a subject in need thereof, a therapeutically-effective amount of a β-lactam antibiotic in conjunction with Hydrate 1.

In one embodiment of the invention, is provided a method of treating or preventing a bacterial infection in a subject comprising the steps of
  a. administering to the subject Hydrate 1; and
  b. administering a therapeutically-effective amount of a β-lactam antibiotic.

In one embodiment of the invention, is provided a method of treating or preventing a bacterial infection in a subject comprising the steps of
  a. administering a therapeutically-effective amount of a β-lactam antibiotic; and
  b. administering to the subject Hydrate 1.

In one embodiment, Hydrate 1, preferably Hydrate 1 in conjunction with a β-lactam antibiotic, can be used to treat a subject having a bacterial infection in which the infection is caused or exacerbated by any type of bacteria, such as Gram-negative bacteria. In one aspect of the invention, the bacterial infection is caused by β-lactamase resistant bacteria. In one aspect the bacterial infection is caused by β-lactamase producing bacteria. In another aspect the bacterial infection is caused by class A, class C or class D β-lactamase producing bacteria. In another aspect the bacterial infection is caused by class A β-lactamase producing bacteria. In another aspect the infection is caused by class C β-lactamase producing bacteria. In still another aspect the infection is caused by class D β-lactamase producing bacteria. In still another aspect the infection is caused by KPC β-lactamase producing bacteria. In still another aspect the infection is caused by OXA β-lactamase producing bacteria.

Representative Gram-negative pathogens known to express β-lactamases include, but are not limited to *Acinetobacter* spp. (including *Acinetobacter baumannii*), *Citrobacter* spp., *Escherichia* spp. (including *Escherichia coli*), *Haemophilus influenzae, Morganella morganii, Pseudomo-* nas aeruginosa, Klebsiella spp. (including Klebsiella pneumoniae), Enterobacter spp. (including Enterobacter cloacae and Enterobacter aerogenes), Pasteurella spp., Proteus spp. (including Proteus mirabilis), Serratia spp. (including Serratia marcescens), and Providencia spp. Bacterial infections can be caused or exacerbated by Gram-negative bacteria including strains which express β-lactamases that may confer resistance to penicillins, cephalosporins, monobactams and/or carbapenems. The co-administration of a novel BLIs that inhibits these β-lactamases with a β-lactam antibiotic could be used to treat infections caused by β-lactam resistant bacteria.

In one aspect of the invention the infection is caused by a β-lactamase producing bacteria selected from *Acinetobacter* spp, *Citrobacter* spp, *Escherichia* coli, *Enterobacter cloacae*), *Haemophilus influenzae, Pseudomonas aeruginosa, Proteus mirabilis, Serratia marcescens*, and *Klebsiella pneumoniae*, β-Lactam antibiotics that may be co-administered with Hydrate 1 include, but are not limited to cephalosporin, carbapenem, monobactam, penem and penicillin classes of antibiotics.

In one embodiment of the invention, the β-lactam antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment of the invention, the β-lactam antibiotic is a carbapenen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In one embodiment of the invention, the β-lactam antibiotic is a monobactam. Examples of monobactam antibiotics include, but are not limited to Aztreonam, Tigemonam, Carumonam, BAL30072 and Nocardicin A.

In one embodiment of the invention, the β-lactam antibiotic is a penem. In one embodiment of the invention, the β-lactam antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

The pharmaceutical compositions, preferably Hydrate 1 in conjunction with a β-lactam antibiotic, can be used to treat a bacterial infection of any organ or tissue in the body caused by β-lactam resistant bacteria, preferably, Gram-negative β-lactam resistant bacteria. These organs or tissue include, without limitation, skeletal muscle, skin, bloodstream, kidneys, heart, lung and bone. For example, a pharmaceutical composition comprising at least Hydrate 1, preferably Hydrate 1 in conjunction with a β-lactam antibiotic, can be administered to a subject to treat, without limitation, skin and soft tissue infections (e.g., complex skin infections), bacteremia, intra-abdominal infections and urinary tract infections (e.g., cUTI). In addition, Hydrate 1 may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. Hydrate 1, preferably Hydrate 1 in conjunction with a β-lactam antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. Hydrate 1, preferably in conjunction with a β-lactam antibiotic, may also be administered to a subject to treat an infection including, without limitation, endocarditis, nephritis, septic arthritis, intra-abdominal sepsis, bone and joint infections and osteomyelitis. Hydrate 1, preferably in conjunction with a β-lactam antibiotic, or pharmaceutical compositions thereof, may also be directly injected or administered into an abscess, ventricle or joint. Pharmaceutical compositions administered as an aerosol for the treatment of pneumonia or other lung-based infections. In one embodiment, the aerosol delivery vehicle is an anhydrous, liquid or dry powder inhaler.

Actual dosage levels of active ingredients in the pharmaceutical compositions of Hydrate 1, preferably Hydrate 1 in conjunction with a β-lactam antibiotic, may be varied so as to obtain a therapeutically-effective amount of the active compound(s) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans. It will be understood by one of skill in the art that the when the composition comprises Hydrate 1 and a β-lactam antibiotic, both Hydrate 1 and the β-lactam antibiotic are active compounds.

The method comprises administering to the subject an effective dose of Hydrate 1, preferably in conjunction with a β lactam antibiotic. An effective dose of Hydrate 1 is generally between 125 mg/day to 2000 mg/day. In one embodiment, an effective dose is from about 0.1 to about 100 mg/kg of Hydrate 1. In one embodiment, the dose is from about 0.1 to about 50 mg/kg of Hydrate 1. In another embodiment, the dose is from about 1 to about 25 mg/kg of Hydrate 1

Hydrate 1, preferably Hydrate 1 in conjunction with a β-lactam antibiotic, may be administered according to this method until the bacterial infection is eradicated or reduced. In one embodiment, Hydrate 1, preferably a compound of Formula in conjunction with a β-lactam antibiotic, are administered for a period of time from 3 days to 6 months. In another embodiment, Hydrate 1, preferably Hydrate 1 in conjunction with a β-lactam antibiotic, are administered for 7 to 56 days. In another embodiment, Hydrate 1, preferably a compound of Hydrate 1 in conjunction with a β-lactam antibiotic, are administered for 7 to 28 days. In a further embodiment, Hydrate 1, preferably Hydrate 1 in conjunction with a β-lactam antibiotic, are administered for 7 to 14 days.

Other embodiments provided herein include:

A pharmaceutical composition comprising Hydrate 1 and at least β-lactam antibiotic or a pharmaceutically acceptable salt thereof.

A pharmaceutical composition comprising Hydrate 1 and at least one cephalosporin antibiotic or a pharmaceutically acceptable salt thereof.

A pharmaceutical composition comprising Hydrate 1 and Ceftolozane antibiotic or a pharmaceutically acceptable salt thereof.

A pharmaceutical composition comprising Hydrate 1 and at least one carbapenem antibiotic or a pharmaceutically acceptable salt thereof.

A pharmaceutical composition comprising Hydrate 1 and at least one monobactam antibiotic or a pharmaceutically acceptable salt thereof.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

EXAMPLES

Example 1

Preparation of sodium (2S,5R)-2-(1,3,4-oxadiazol-2-yl)-7-oxo-1,6-diazabicyclo[3.2.1]octan-6-yl sulfate Synthesis of (2S,5R)-ethyl 6-(benzyloxy)-7-oxo-1,6-diazabicyclo[3.2.1]octane-2-carboxylate (Intermediate Compound 1)

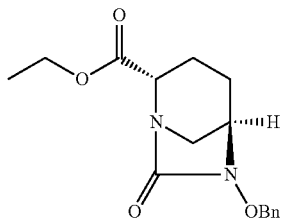

Step 1: Synthesis of (S)-1-tert-butyl 2-ethyl 5-oxopiperidine-1,2-dicarboxylate

Method A:

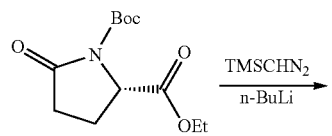

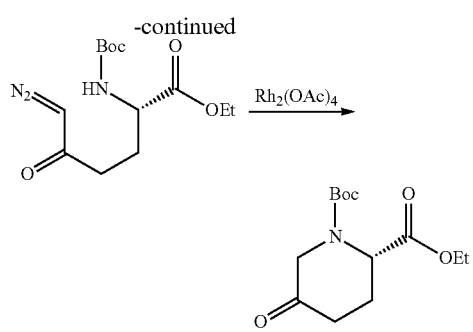

n-BuLi (600 mL, 1.5 mol) was added dropwise to a solution of TMSCHN$_2$ (690 mL, 1.38 mol) in dry THF (3 L) at −78° C., and the mixture was stirred at −78° C. for 30 minutes. The mixture was then transferred to a solution of (S)-1-tert-butyl 2-ethyl 5-oxopyrrolidine-1,2-dicarboxylate (300 g, 1.17 mol) in dry THF (3 L) via cannula, and the mixture was stirred at −78° C. for 30 minutes. The reaction mixture was then quenched with sat. NH$_4$Cl solution, and extracted with DCM (3×). The combined organic layer was concentrated under reduced pressure and the crude product was purified by silica gel column chromatography (3:1 petroleum ether:EtOAc) to afford (S)-ethyl 2-((tert-butoxycarbonyl)amino)-6-diazo-5-oxohexanoate (262 g, 75%) as a yellow solid.

A solution of (S)-ethyl 2-((tert-butoxycarbonyl)amino)-6-diazo-5-oxohexanoate (350 g, 1.18 mol) in DCM (1500 mL) was added to a solution of Rh$_2$(OAc)$_4$ (3.5 g, 7.9 mmol) in DCM (750 mL) at 0° C. The reaction was then stirred at 20° C. overnight and then concentrated in vacuum. The crude sample was purified by silica gel column chromatography (5:1 petroleum ether/EtOAc) to afford (S)-1-tert-butyl 2-ethyl 5-oxopiperidine-1,2-dicarboxylate (175.9 g, 55%) as a yellow oil.

Method B:

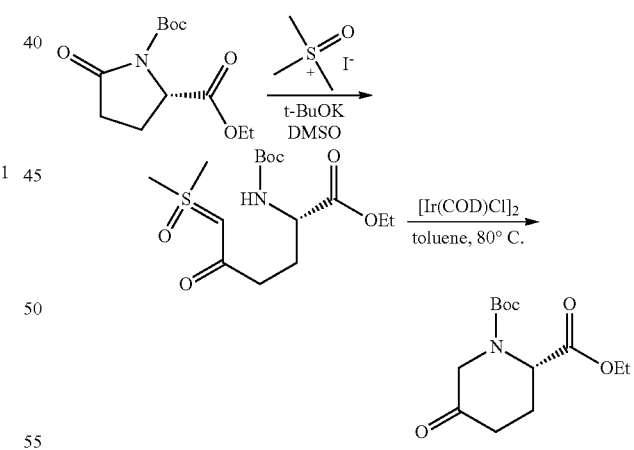

t-BuOK (330 g, 2.9 mol) was added to a solution of trimethylsulfoxonium iodide (750 g, 3.5 mol) in dry DMSO (3 L) and the mixture was stirred at rt for 1 h. (S)-1-tert-Butyl 2-ethyl 5-oxopyrrolidine-1,2-dicarboxylate (900 g, 3.5 mol) was added and the mixture was stirred at rt for 2-3 hrs. Water was added to quench the reaction and the mixture was extracted with EtOAc (5×). The combined organic layer was concentrated in vacuum and the crude sample was purified by silica gel column chromatography (1:1 petroleum ether/EtOAc then 1:10 MeOH/DCM) to afford sulfoxonium ylide intermediate (977 g, 80%) as a white solid.

A solution of sulfoxonium ylide intermediate (156 g, 0.446 mol) and [Ir(COD)Cl]$_2$ (3 g, 4.46 mmol) in toluene (4 L) was degassed by bubbling nitrogen through the solution for 10 minutes. The reaction mixture was heated to 80-90° C. for 2-3 hrs and then cooled to 20° C. Then toluene was concentrated under reduced pressure, the residue was purified by silica gel column chromatography (10:1 to 3:1 gradient petroleum ether/EtOA) to afford (S)-1-tert-butyl 2-ethyl 5-oxopiperidine-1,2-dicarboxylate (140 g, 57.8%) as a yellow oil.

Step 2: Synthesis of (2S,5S)-1-tert-butyl 2-ethyl 5-hydroxypiperidine-1,2-dicarboxylate

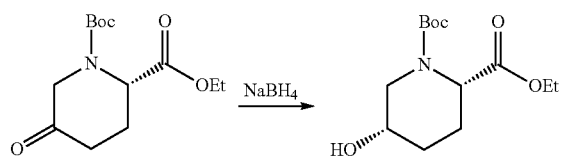

NaBH$_4$ (36 g, 1.0 mol) was added in portions to a solution of (S)-1-tert-butyl 2-ethyl 5-oxopiperidine-1,2-dicarboxylate (250 g, 0.92 mol) in EtOH (1500 mL) at −40° C. The reaction mixture was then stirred at −40° C. for 0.5 hr then quenched with 10% HOAc solution. After diluting with water, the mixture was extracted with DCM (3×). The combined organic layer was concentrated in vacuum and purified by silica gel column chromatography (1:1 petroleum ether/EtOAc) to afford (2S,5S)-1-tert-butyl 2-ethyl 5-hydroxypiperidine-1,2-dicarboxylate (205 g, 80%) as a yellow oil.

Step 3: Synthesis of (2S,5R)-1-tert-butyl 2-ethyl 5-(N-(benzyloxy)-2-nitrophenylsulfonamido)piperidine-1,2-dicarboxylate

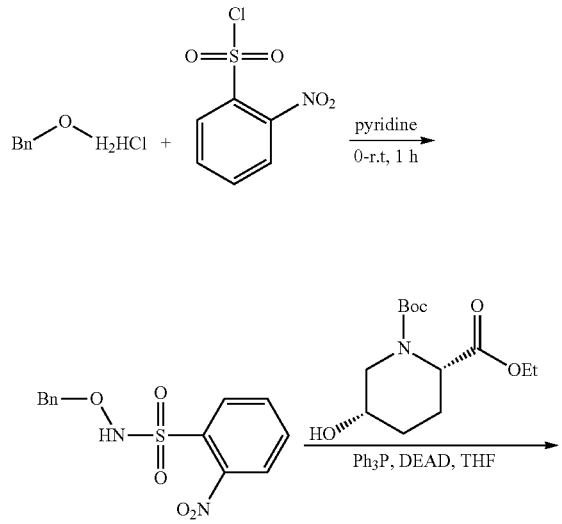

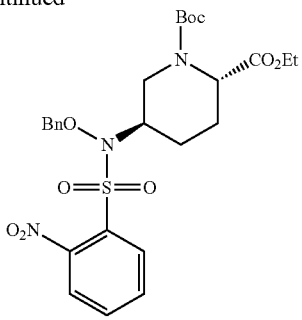

A solution of 2-nitrobenzene-1-sulfonyl chloride (500 g, 2.26 mol) in pyridine (1500 mL) was added dropwise to a solution of O-benzylhydroxylamine hydrochloride (400 g, 2.51 mol) in pyridine (1500 mL) at 0° C. The reaction mixture was then stirred at 20° C. overnight. The mixture was concentrated in vacuum, diluted with DCM and washed with HCl (10%) three times. The combined organic layer was concentrated under reduced pressure and re-crystallized with DCM to afford N-(benzyloxy)-2-nitrobenzenesulfonamide (485 g, 62.6%) as a yellow solid.

To a solution of N-(benzyloxy)-2-nitrobenzenesulfonamide (212 g, 0.69 mol) in THF (1000 mL) was added (2S, 5S)-1-tert-butyl 2-ethyl 5-hydroxypiperidine-1,2-dicarboxylate (171 g, 0.63 mol) and PPh$_3$ (275 g, 1.05 mol), followed by dropwise addition of a solution of DEAD (195 g, 1.12 mol) in THF (500 mL). The mixture was then stirred at 20° C. overnight. The reaction mixture was then concentrated in vacuum and purified by silica gel column chromatography (3:1 petroleum ether/EtOAc) to afford (2S,5R)-1-tert-butyl 2-ethyl 5-(N-(benzyloxy)-2-nitrophenylsulfonamido)piperidine-1, 2-dicarboxylate (283.8 g, 80%) as a yellow oil.

Step 4: Synthesis of (2S,5R)-1-tert-butyl 2-ethyl 5-((benzyloxy)amino)piperidine-1,2-dicarboxylate

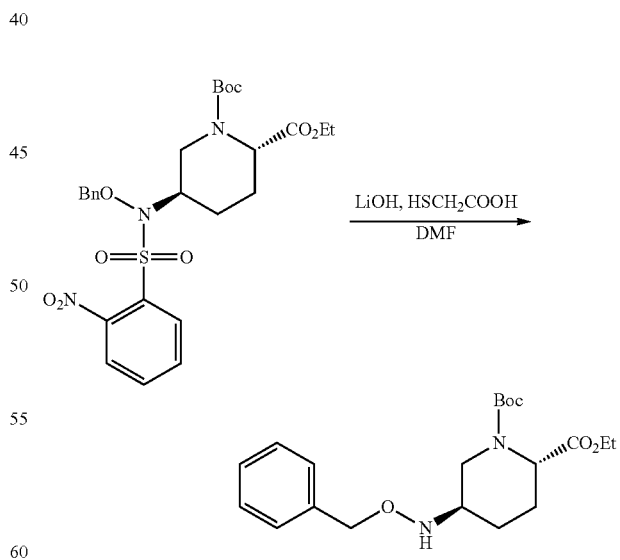

LiOH.H$_2$O (95 g, 2.3 mol) and 2-mercaptoacetic acid (124 g, 1.3 mol) were added to a solution of (2S,5R)-1-tert-butyl 2-ethyl 5-(N-(benzyloxy)-2-nitrophenylsulfonamido)piperidine-1,2-dicarboxylate (251 g, 0.45 mol) in DMF (1200 mL). The reaction mixture was then stirred at 20° C. overnight. The reaction mixture was diluted with water and extracted with EtOAc (3×). The combined organic layer was washed with brine (3×), concentrated under reduced pressure and purified by silica gel column chromatography (3:1 petroleum ether/EtOAc) to afford (2S,5R)-1-tert-butyl 2-ethyl 5-((benzyloxy)amino)piperidine-1,2-dicarboxylate (122.9 g, 85%) as a yellow solid.

Step 5: Synthesis of (2S,5R)-ethyl 5-((benzyloxy)amino)piperidine-2-carboxylate

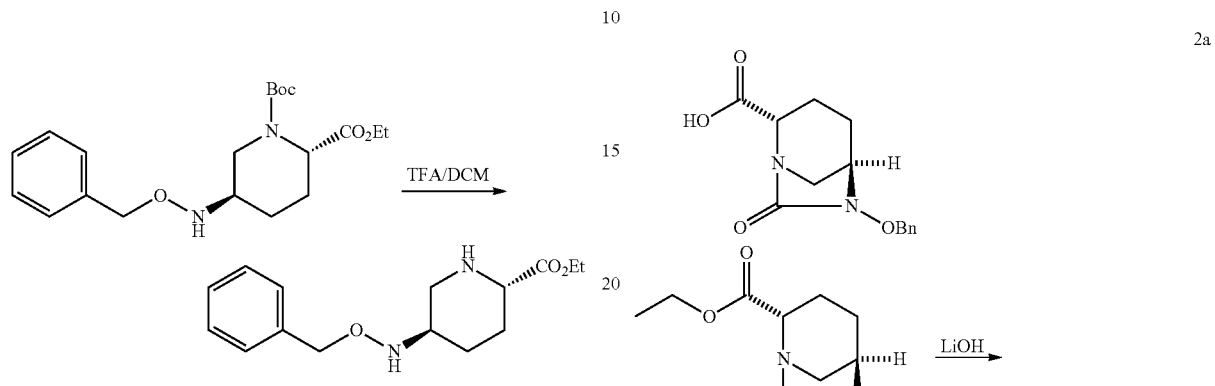

TFA (600 mL) was added to a solution of (2S,5R)-1-tert-butyl 2-ethyl 5-((benzyloxy)amino)piperidine-1,2-dicarboxylate (263 g, 0.7 mol) in DCM (600 mL) at 20° C. The mixture was stirred at rt overnight and then concentrated in vacuum. The crude product was adjusted to pH 10 with sat. NaHCO₃ solution, and then extracted with DCM three times. The combined organic layer was concentrated in vacuum and purified by silica gel column chromatography (20:1 DCM/MeOH) to afford (2S,5R)-ethyl 5-((benzyloxy)amino)piperidine-2-carboxylate (184.9 g, 95%) as a yellow oil.

Step 6: Synthesis of (2S,5R)-ethyl 6-(benzyloxy)-7-oxo-1,6-diazabicyclo[3.2.1]octane-2-carboxylate

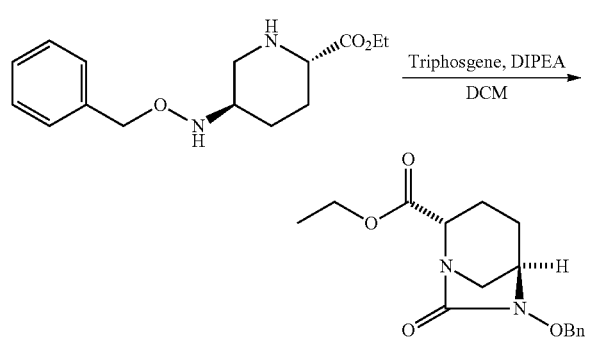

Triphosgene (21.3 g, 72 mmol) was added in portions to a solution of (2S,5R)-ethyl 5-((benzyloxy)amino)piperidine-2-carboxylate (50 g, 0.18 mol) and DIPEA (128 mL, 0.72 mol) in DCM (2000 mL) at 0° C. After stirring at 20° C. overnight, the reaction mixture was washed with $H_3PO_4$ (10%), sat. NaHCO₃ and saturated NaCl. The combined organic layer was concentrated under reduced pressure and purified by silica gel column chromatography (3:1 petroleum ether/EtOAc) to afford (2S,5R)-ethyl 6-(benzyloxy)-7-oxo-1,6-diazabicyclo[3.2.1]octane-2-carboxylate (27.4 g, 50%) as a yellow solid. ¹H NMR (400 Mz, CDCl₃): δ 7.43-7.36 (m, 5H), 5.06 (d, J=11.4 Hz, 1H), 4.90 (d, J=11.4 Hz, 1H), 4.24 (q, J=7.1 Hz, 2H), 4.11-4.08 (m, 1H), 3.32-3.31 (m, 1H), 3.08-3.05 (m, 1H), 2.93 (d, J=11.9 Hz, 1H), 2.14-2.05 (m, 2H), 2.05-2.00 (m, 1H), 1.71-1.63 (m, 1H), 1.29 (t, J=7.1 Hz, 3H).

Synthesis of (2S,5R)-6-(benzyloxy)-7-oxo-1,6-diazabicyclo[3.2.1]octane-2-carboxylic acid (Intermediate Compound 2a)

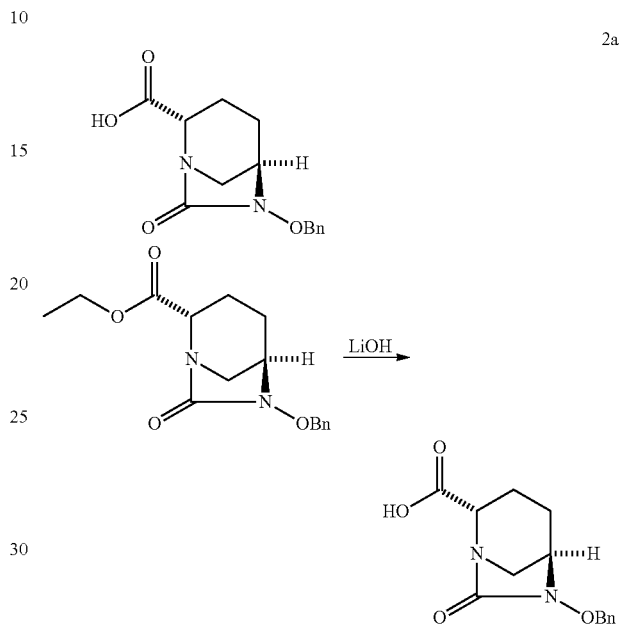

LiOH (1.2 g, 29.6 mmol) was added to a solution of (2S,5R)-ethyl 6-(benzyloxy)-7-oxo-1,6-diazabicyclo[3.2.1]octane-2-carboxylate (9 g, 29.6 mmol) in $THF/H_2O$ (3:1, 240 mL). The mixture was then stirred at rt overnight. The reaction mixture was washed with EtOAc twice, then the aqueous solution was adjusted pH 2-3 with 1N HCl. The resulting mixture was extracted with DCM three times, and the combined organic layer was dried over saturated $Na_2SO_4$ and concentrated under reduced pressure to provide (2S,5R)-6-(benzyloxy)-7-oxo-1,6-diazabicyclo[3.2.1]octane-2-carboxylic acid (7.0 g, 77.7%), which was directly used in the next step without further purification. ESI-MS (EI⁺, m/z): 277.31. ¹H NMR (300 MHz, CDCl₃) δ 7.49-7.29 (m, 5H), 5.06 (d, J=11.4 Hz, 1H), 4.91 (d, J=11.4 Hz, 1H), 4.15-4.10 (m, 1H), 3.36-3.34 (m, 1H), 3.15-3.11 (m, 1H), 2.83 (d, J=11.8 Hz, 1H), 2.32-2.15 (m, 1H), 2.11-2.01 (m, 2H), 1.74-1.56 (m, 1H).

Synthesis of sodium (2S,5R)-2-(1,3,4-oxadiazol-2-yl)-7-oxo-1,6-diazabicyclo[3.2.1]octan-6-yl sulfate

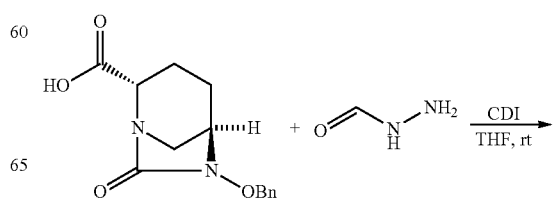

-continued

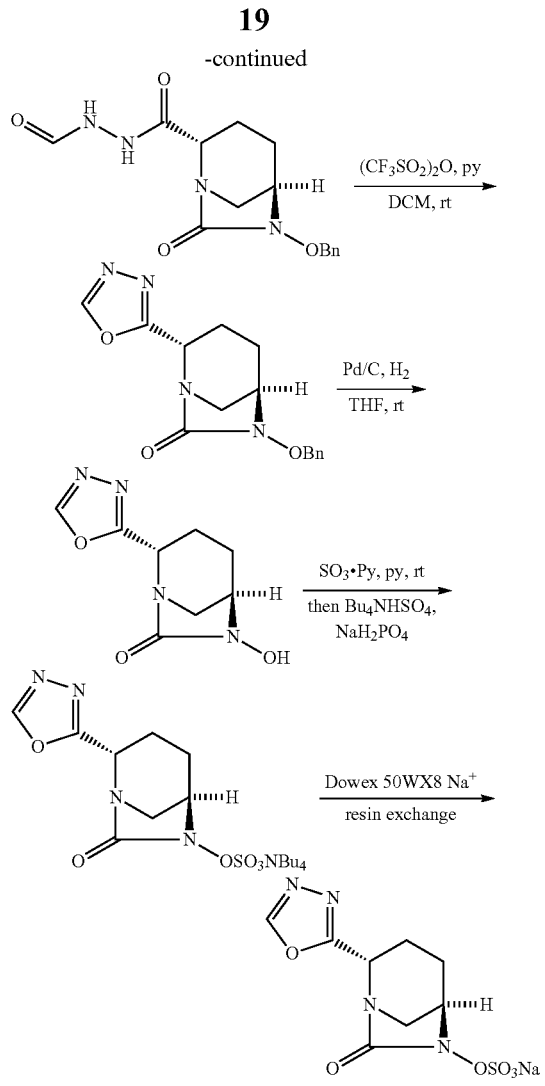

Step 1:

1,1'-Carbonyldiimidazole (5.8 g, 36.2 mmol) was added to a solution of (2S,5R)-6-(benzyloxy)-7-oxo-1,6-diazabicyclo[3.2.1]octane-2-carboxylic acid (5.0 g, 18.1 mmol) in dry THF (200 mL) at 0° C. The reaction mixture was stirred at rt for 3 hrs. Formohydrazide (5.4 g, 90.5 mmol) was added in one portion, and the reaction mixture was stirred for additional 3 hrs. The mixture was then diluted with brine and exacted with EtOAc (3×). The combined organic layer was washed with Saturated sodium chloride (2×), dried over $Na_2SO_4$, and concentrated to afford crude (2S,5R)-6-(benzyloxy)-N'-formyl-7-oxo-1,6-diazabicyclo[3.2.1]octane-2-carbohydrazide (~11 g), which was directly used in the next step. ESI-MS (EI$^+$, m/z): 319.1 [M+H]$^+$.

Step 2:

To a solution of (2S,5R)-6-(benzyloxy)-N'-formyl-7-oxo-1,6-diazabicyclo[3.2.1]octane-2-carbohydrazide (11 g) in dry DCM (200 mL) at −10° C. was added pyridine (28 mL), followed by dropwise addition of $(CF_3SO_2)_2O$ (28 mL). The reaction mixture was allowed to warm to rt and was stirred for 3 hrs. The reaction mixture was then cooled to −10° C. and quenched with sat. $NaHCO_3$. The organic layer was separated and the aqueous layer was extracted with EtOAc (3×). The combined organic layer was dried over $Na_2SO_4$, concentrated and purified by silica gel column chromatography (gradient elution 1:3 to 2:1 EtOAc/hexanes) to give (2S,5R)-6-(benzyloxy)-2-(1,3,4-oxadiazol-2-yl)-1,6-diazabicyclo[3.2.1]octan-7-one (4.6 g, 86% for two steps) as a slight yellow solid. ESI-MS (EI$^+$, m/z): 301.0 [M+H]$^+$.

Step 3:

To a solution of (2S,5R)-6-(benzyloxy)-2-(1,3,4-oxadiazol-2-yl)-1,6-diazabicyclo[3.2.1]octan-7-one (4.6 g, 15.3 mmol) in THF (150 mL) was added 10% Pd/C (1 g). The mixture was stirred under $H_2$ atmosphere at rt for 3 hrs. The reaction mixture was then filtered and concentrated to afford (2S,5R)-6-hydroxy-2-(1,3,4-oxadiazol-2-yl)-1,6-diazabicyclo[3.2.1]octan-7-one (2.9 g, 91%), which was used directly in the next step. ESI-MS (EI$^+$, m/z): 211.1 [M+H]$^+$.

Step 4:

To a solution of (2S,5R)-6-hydroxy-2-(1,3,4-oxadiazol-2-yl)-1,6-diazabicyclo[3.2.1]octan-7-one (2.9 g, 13.8 mmol) in dry pyridine (60 mL) was added $SO_3$·Py (11.0 g, 69.0 mmol). The reaction mixture was stirred at rt for 8 hrs and then concentrated under vacuum. The residue was re-dissolved in aqueous $NaH_2PO_4$ (1.5 M, 100 mL) then tetrabutylammonium hydrogensulphate (5.88 g, 17.3 mmol) was added. The mixture was stirred at rt for 20 minutes, then extracted with EtOAc (4×). The combined organic layer was dried and concentrated and the residue was purified by silica gel column chromatography (gradient elution 10:1 to 2:1 DCM/acetone) to afford tetrabutylammonium (2S,5R)-2-(1,3,4-oxadiazol-2-yl)-7-oxo-1,6-diazabicyclo[3.2.1]octan-6-yl sulfate (4.1 g, 97%) as a white solid. ESI-MS (EI$^-$, m/z): 289.0 [M−H]$^-$. $^1$H-NMR (400 MHz, $CDCl_3$): δ 8.48 (s, 1H), 4.75 (d, J=6.5 Hz, 1H), 4.40 (br s, 1H), 3.34-3.26 (m, 9H), 2.82 (d, J=12.0 Hz, 1H), 2.37-2.25 (m, 3H), 2.06-1.98 (m, 1H), 1.71-1.65 (m, 8H), 1.49-1.42 (m, 8H), 1.01 (t, J=7.5 Hz, 12H).

Step 5:

Resin Exchange: Tetrabutylammonium (2S,5R)-2-(1,3,4-oxadiazol-2-yl)-7-oxo-1,6-diaza-bicyclo[3.2.1]octan-6-yl sulfate (4.1 g, 7.72 mmol) was dissolved in a minimum amount of HPLC grade water (~40 mL) and passed through a column of 80 g of DOWEX 50WX 8 Na$^+$ resin (the resin was prewashed with >4 L of HPLC grade water) and eluted with HPLC grade water to afford sodium (2S,5R)-2-(1,3,4-oxadiazol-2-yl)-7-oxo-1,6-diazabicyclo[3.2.1]octan-6-yl sulfate (2.2 g, 91%) as a white solid after lyophilization. ESI-MS (EI$^+$, m/z): 291.2 [M+H]$^+$. $^1$H NMR (300 MHz, $D_2O$) δ 8.92 (s, 1H), 4.84 (d, J=6.7 Hz, 1H), 4.20 (br s, 1H), 3.25-3.16 (m, 1H), 2.92 (d, J=12.3 Hz, 1H), 2.41-2.26 (m, 1H), 2.26-2.11 (m, 2H), 2.04-1.89 (m, 1H).

Example 2

Procedure for Preparing Hydrate 1

Campaign Equipment

5 L glass jacketed, stirred reactor with two staged impellers (5" OD high viscosity [lower] and 4" OD 60° [upper])

50 L glass jacketed, stirred reactor with two staged impellers (5" OD high viscosity [lower] and 4" OD 60° [upper])

Continuous filtration system consisting of: a HDPE table-top Buchner funnel 18" ID; HDPE 20" OD top with hose barb on top and Y-fitting underneath; 18" flange gasket sandwiched between Buchner and top; HDPE tubing with 0.6" ID and 0.75" OD; HDPE NPT to hose barb fittings; 20 L vacuum filter flask To effect continuous filtration, the slurry is gravity-fed from the bottom of the SOL reactor to the filter top while the filtrate is piped to the vacuum filter flask Material Requirements Provided below is the way to calculate required material masses based on the input of anhydrous sodium (2S,5R)-2-

(1,3,4-oxadiazol-2-yl)-7-oxo-1,6-diazabicyclo[3.2.1]octan-6-yl sulfate ("A"). For instance, if A=1.00 kg, then the amount of WFI water (water for injection) required is 1.00*1.93=1.93 kg.

Material Requirements

| Item | Ratio |
|---|---|
| Anhydrous Na Salt | A |
| THF (solution) | 1.77 |
| WFI water (solution) | 1.93 |
| THF (antisolvent) | 31.69 |
| THF (wash) | 4.28 |
| WFI water (wash) | 0.18 |

Feed Solution Preparation

| 1 | Charge to 5 L reactor 1.10 kg of sodium (2S,5R)-2-(1,3,4-oxadiazol-2-yl)-7-oxo-1,6-diazabicyclo[3.2.1]octan-6-yl sulfate |
|---|---|
| 2 | Charge to 5 L reactor 2.12 kg of WFI water<br>Note: sodium (2S,5R)-2-(1,3,4-oxadiazol-2-yl)-7-oxo-1,6-diazabicyclo[3.2.1]octan-6-yl sulfate and water were charged in alternating portions because of the very low bulk density of this compound |
| 3 | Charge to 5 L reactor 1.94 kg of tetrahydrofuran |
| 4 | Stir system at 150-200 rpm until a clear solution is obtained (approx. 15-20 min.) |

Recrystallization, Filtration, and Wash

| 1 | Charge to 50 L reactor 5.10 kg of feed solution (98.8% of original system)<br>Note: The feed solution was a deep, golden-yellow color |
|---|---|
| 2 | Set reactor to stir at 92-95 rpm |
| 3 | Charge by vacuum 34.56 kg of tetrahydrofuran.<br>Note: Addition rate targeted at 2.2 kg/min, but actual addition rate was ~5.8 kg/min. Addition by vacuum was difficult to control precisely since a minimum amount of vacuum was needed to provide sufficient pressure head to get liquid out of the drum.<br>Note: Crystals are observed almost immediately after addition begins.<br>Note: Some THF seen condensing on condenser below point where vacuum was drawn.<br>Note: This step represents the maximum volume of approximately 47 L. |
| 4 | Let stir for 2.5 hours |
| 5 | Filter product. Vacuum downstream of filter flask was opened first, then the bottom valve was opened to feed slurry by gravity to filter.<br>Note: ~300 mL of solvent was collected in cold trap downstream of filter flask<br>Note: The mother liquors were a light yellow color<br>Note: The filtration was fast and smooth. |
| 5 | Wash cake with 4.84 kg wash solvent. Smooth out cake, then draw vacuum to filter.<br>Note: Wash solvent = 4.65 kg tetrahydrofuran + 0.20 kg WFI water; prepared in advance<br>Note: The amount of water in the wash solvent should be no more than 5% of the total wash mass |
| 6 | The isolated mass was 1.082 kg of Hydrate 1 in 88.0% molar yield |

Example 3

Polymorph Studies

Described herein are polymorphism studies carried out on sodium (2S,5R)-2-(1,3,4-oxadiazol-2-yl)-7-oxo-1,6-diazabicyclo[3.2.1]octan-6-yl sulfate. A number of different conditions, including a diverse range of solvent systems and temperature profiles, were used during this investigation. In summary, seven different hydrated crystalline forms were identified for this salt.

Solid state characterisation was performed on five of the seven forms, together with an assessment of stability relationships between the different hydrates. The remaining forms could not be isolated due to their metastable nature.

Based on these findings, it was concluded that Hydrate 1 is the most stable crystalline form at ambient conditions (25° C. and 40% RH) (see FIG. 2).

X-Ray Powder Diffraction (XRPD)
Bruker AXS D8 Advance

X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: angular range: 2 to 42 °2θ; step size: 0.05 °2θ; collection time: 0.5 s/step.

Differential Scanning Calorimetry (DSC)

DSC data were collected on a Mettler DSC 823E equipped with a 34 position auto-sampler. The instrument was calibrated for energy and temperature using certified indium. Typically 0.5-3 mg of each sample, in a pin-holed aluminium pan, was heated at 10° C./min from 25° C. to 300° C. A nitrogen purge at 50 ml/min was maintained over the sample.

The instrument control and data analysis software was STARe v9.20.

Thermo-Gravimetric Analysis (TGA)

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 10° C./min from ambient temperature to 350° C. A nitrogen purge at 50 ml/min was maintained over the sample.

The instrument control and data analysis software was STARe v9.20.

FIG. 3 depicts the differential scanning calorimetry (DSC) thermogram and the thermogravimetry curve of Hydrate 1.

Gravimetric Vapour Sorption (GVS)

Sorption isotherms were obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range Data analysis was undertaken in Microsoft Excel using DVS Analysis Suite v6.2 (or 6.1 or 6.0).

Method Parameters for SMS DVS Intrinsic Experiments

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

FIG. 4 depicts the DVS graph of amorphous sodium (2S, 5R)-2-(1,3,4-oxadiazol-2-yl)-7-oxo-1,6-diazabicyclo[3.2.1] octan-6-yl sulfate. In contrast, FIG. 5 depicts the DVS graph of Hydrate 1. As can be seen, Hydrate 1 is significantly less hygroscopic than the amorphous form of this compound.

Polymorphism Studies

Screen Procedure and Results

A wide range of methodologies was used in an attempt to fully evaluate the polymorphic landscape of the sodium salt. These include traditional crystallisation, slow evaporation, heat/cool cycles and suspension/equilibration techniques. Slurry ripening or slurry maturation increases the possibility of generating metastable forms in accordance with the Ostwald rule of stages (Ostwald, W. (1897). "Studien über die Bildung und Umwandlung fester Körper. 1. Abhandlung: Übersättigung und Überkaltung". Zeitschrift für Physikalische Chemie 22: 289-330).

Procedure 1:

Sodium (2S,5R)-2-(1,3,4-oxadiazol-2-yl)-7-oxo-1,6-diazabicyclo[3.2.1]octan-6-yl sulfate (~40 mg) was dissolved in 400 μL of water and the resulting clear solution was freeze-dried to generate amorphous material (a control sample was analysed by XRPD to ensure that the freeze dry material was completely amorphous). Different solvent systems were then added to the amorphous material in 5 vol. portions until a clear solution was obtained or 50 vol. had been used. Slurries were split in two sets; the first one was stirred at 50° C. (a) while the second one was stirred at 4° C. (b) for 3 days. Clear solutions were also split in two sets, the first one was allowed to slowly evaporate (c) and the second one was placed at 4° C. (d). All residual solids were filtered, air dried and analysed by XRPD. The results are summarized in Table 1.

Procedure 2:

Amorphous material (~40 mg) was generated as in Procedure 1. Different solvents systems (2 mL) were added and the resulting slurries were subjected to heat/cool cycles 25/50° C. (two hours at each temperature and ramps of 0.5° C./min) for 3 days. All residual solids were filtered, air dried and analysed by XRPD. The results are summarized in Table 1.

Procedure 3:

A few experiments were repeated following Procedure 1a, with samples being analyzed after 3 h, 24 h, and 48 h. The final product was filtered after 120 h. The solids isolated were analysed by XRPD. The results are summarized in Table 2.

Procedure 4:

Amorphous material (~60 mg) was generated as in Procedure 1. The amorphous material was suspended in different solvent systems (3 mL) at 50° C. A sample was withdrawn after 3 h and 24 h. The final product was filtered after 48 h and analysed by XRPD. The solids isolated were re-analysed again by XRPD after few days at ambient conditions (~25° C. and ~40% RH). The results are summarized in Table 2.

Procedure 5:

Amorphous material (~100 mg) was generated as in Procedure 1. The amorphous material was split in two portions (~50 mg each) and suspended in IPA/water (98:2) (2 mL). The first set of experiments (a) was subjected to heat/cool cycles as described in Procedure 2 and the second set of experiments (b) was stirred at 50° C. A sample was withdrawn after 3 h and 24 h. The final product was filtered after 48 h, dried under nitrogen current and analysed by XRPD. The results are summarized in Table 2.

Table 1 shows the results of the initial screen where the crystalline forms were identified and denoted Hydrate 1, Hydrate 2, Hydrate 3, Hydrate 4, Hydrate 5 and Hydrate 7.

TABLE 1

Results from Polymorphism Screen (Procedures 1 and 2)

| Solvent | Procedure | Observation | Result |
|---|---|---|---|
| Heptane | 1a | Suspension | Mainly Amorphous |
| Heptane | 1b | Gum | N/A |
| Cumene | 1a | Suspension | Mainly Amorphous |
| Cumene | 1b | Gel | N/A |
| Anisole | 1a | Suspension | Hydrate 1 |
| Anisole | 1b | Suspension | Hydrate 1 |
| Ethyl Acetate | 1a | Suspension | Hydrate 1 + extra peaks |
| Ethyl Acetate | 1b | Suspension | Hydrate 1 |
| Isopropyl Acetate | 1a | Suspension | Hydrate 1 |
| Isopropyl Acetate | 1b | Suspension | Hydrate 1 |
| Methylisobutyl Ketone | 1a | Suspension | Hydrate 1 |
| Methylisobutyl Ketone | 1b | Suspension | Hydrate 1 |
| 2-Propanol | 1a | Suspension | Hydrate 1 |
| 2-Propanol | 1b | Suspension | Hydrate 1 |
| Methylethyl Ketone | 1a | Suspension | Hydrate 1 |
| Methylethyl Ketone | 1b | Suspension | Hydrate 1 |
| Acetone | 1c | Powder | Hydrate 1 |
| Acetone | 1d | Clear solution | N/A |
| Dimethyl Sulfoxide | 1c | Gum | N/A |
| Dimethyl Sulfoxide | 1a | Suspension | Hydrate 1 |
| t-Butylmethyl Ether | 1b | Suspension | Hydrate 1 |
| 1-4-Dioxane | 1a | Suspension | Mainly amorphous |
| Toluene | 1a | Slurry | Hydrate 1 |
| Toluene | 1b | Gel | N/A |
| Tetralin | 1a | Slurry | Mainly amorphous |
| Tetralin | 1b | Gel | N/A |
| 1-2-Dimethoxyethane | 1a | Slurry | Hydrate 3 |
| Tetrahydrofuran | 1a | Slurry | Hydrate 1 + Hydrate 3 |
| Tetrahydrofuran | 1b | Slurry | Hydrate 1 |
| Dichloromethane | 1a | Slurry | Hydrate 1 + Hydrate 4 |
| Dichloromethane | 1b | Slurry | Hydrate 1 |
| DMF | 1c | Gel | N/A |
| DMF | 1d | Clear solution | N/A |
| Acetonitrile | 1c | Powder | Hydrate 1 |
| Acetonitrile | 1b | Slurry | Hydrate 1 |
| Nitromethane | 1a | Slurry | Hydrate 1 + extra peaks |
| Ethylene glycol | 1a | Slurry | Pattern 1 |
| Water:THF (2:98) | 1a | Oil | N/A |
| Water:THF (2:98) | 1b | Slurry | Hydrate 1 |

TABLE 1-continued

Results from Polymorphism Screen (Procedures 1 and 2)

| Solvent | Procedure | Observation | Result |
|---|---|---|---|
| Water:IPA (2:98) | 1a | Slurry | Hydrate 1 + Hydrate 7 |
| Water:IPA (2:98) | 1b | Slurry | Hydrate 1 |
| Water:Acetone (2:98) | 1c | Powder | Hydrate 1 |
| Water:Acetone (2:98) | 1d | Big crystals | Hydrate 1 |
| THF | 2 | Slurry | Hydrate 1 |
| DCM | 2 | Slurry | Hydrate 1 |
| Nitromethane | 2 | Slurry | Hydrate 1 |
| Acetone | 2 | Slurry | Hydrate 1 |
| IPA | 2 | Slurry | Hydrate 1 |
| IPA/water (95:5) | 2 | Slurry | Hydrate 1 |
| IPA/water (90:10) | 2 | Slurry | Hydrate 1 |
| IPA/water (80:20) | 2 | Clear solution | Hydrate 2 |
| Ethyl Acetate | 2 | Slurry | Hydrate 1 + extra peaks |
| IPA/water (99.5:0.5) | 2 | Slurry | Hydrate 1 |
| IPA/water (99:1) | 2 | Slurry | Hydrate 1 |
| IPA/water (98:2) | 2 | Slurry | Hydrate 5 |

Table 2 shows the results from experiments in which samples were taken at different times to identify new metastable forms; crystalline Hydrate 6 was identified during these experiments.

TABLE 2

Results from Polymorphism Screen (Procedures 3, 4 and 5)

| Solvent | Vol. | Procedure | 3 h | 24 h | 48 h | 120 h |
|---|---|---|---|---|---|---|
| EtOAc | 50 | 3 | H1 | H1 + H5 | H1 | H1 |
| DME | 50 | 3 | H1 | H1 + H5 | Amorphous | Amorphous |
| DCM | 50 | 3 | H1 | H1 + H4 | H1 + H4 | H1 |
| Nitromethane | 50 | 3 | H1 + H5 | Amorphous | N/A | H1 |
| IPA | 50 | 3 | H1 + H5 | H1 + H5 | H1 + H5 | H1 |
| IPA/H$_2$O (98.5:1.5) | 50 | 3 | H1 + H5 | H1 + H5 | H5 + extra peaks | H1 |
| IPA/H$_2$O (98:2) | 50 | 3 | H1 + H5 | H1 + H5 | H1 + H5 | H1 |
| IPA/H$_2$O (97.5:2.5) | 50 | 3 | H1 + H5 | H1 + H5 | H5 + H1 | H1 |
| Acetone/H$_2$O (98.5:1.5) | 25 | 3 | H1 | H1 + H5 | H1 + H5 | H1 |
| Acetone/H$_2$O (98:2) | 25 | 3 | Clear solution obtained, no further analyses carried out. | | | |
| Acetone/H$_2$O (97.5:2.5) | 25 | 3 | Clear solution obtained, no further analyses carried out. | | | |
| IPA | 50 | 4 | H1 + H4 | H3 | H5 | N/A |
| IPA/H$_2$O (98:2) | 50 | 4 | H5 + H6 | H6 + H5 | H6 + H1 | N/A |
| DME | 50 | 4 | H4 | H4 | H4 | N/A |
| DCM | 50 | 4 | H4 | H4 | H4 + H1 | N/A |
| IPA/H$_2$O (98:2) | 40 | 5a | H5 + H1 | H5 + H1 | H5 | N/A |
| IPA/H$_2$O (98:2) | 40 | 5b | H5 + H1 | H5 + H1 | H5 | N/A |

Table 3 shows the re-analyses of some samples after storage at ambient conditions. From these results can be observed that Hydrate 4 is metastable and transforms to Hydrate 1; Hydrate 3 and Hydrate 6 are also metastable and transform to Hydrate 5 or Hydrate 1 at ambient conditions.

TABLE 3

Results from the Re-analysis of Samples

| XRPD | Conditions | XRPD |
|---|---|---|
| H1 + H4 | 48 h a.c. | H1 |
| H5 + H6 | 48 h a.c. | H5 + H1 |
| H4 | 48 h a.c. | H1 + extra peaks |
| H4 | 48 h a.c. | H1 |
| H3 | 24 h a.c. | H3 + H5 |
| H6 + H5 | 24 h a.c. | H5 + H6 |
| H4 | 24 h a.c. | H5 |
| H4 | 24 h a.c. | H1 + H5 |
| H5 | 72 h a.c. | H5 |
| H6 + H1 | 72 h a.c. | H6 + H1 |
| H4 | 72 h a.c. | H5 |
| H4 + H1 | 72 h a.c. | H4 + H5 + H1 |

H: Hydrate; a.c.: ambient conditions.

Drying Experiments

In order to understand the minimum amount of water required to obtain pure Hydrate 1 material, with no contamination from other hydrated forms, a series of experiments were carried out to investigate the effect of the water activity in the hydration level of sodium (2S,5R)-2-(1,3,4-oxadiazol-2-yl)-7-oxo-1,6-diazabicyclo[3.2.1]octan-6-yl sulfate. Sodium (2S,5R)-2-(1,3,4-oxadiazol-2-yl)-7-oxo-1,6-diazabicyclo[3.2.1]octan-6-yl sulfate was placed at the vacuum oven over the weekend at 70° C. and 5 mBar. The resulting amorphous material was suspended in different solvent systems and stirred at 25° C. for 24 hours. The solids were then filtered and analysed by XRPD (see Table 4 for details).

TABLE 4

Water Activity (a$_w$) Results

| Na Salt | Solvent | % water | mL | Water activity | XRPD |
|---|---|---|---|---|---|
| 40 | THF | 0.0 | 1.0 | 0 | Mainly amorphous |
| 40 | THF | 0.2 | 1.0 | 0.11 | Hydrate 5 |
| 40 | THF | 0.4 | 1.0 | 0.20 | Hydrate 5 |

TABLE 4-continued

Water Activity (a_w) Results

| Na Salt | Solvent | % water | mL | Water activity | XRPD |
|---|---|---|---|---|---|
| 20 | THF | 0.6 | 0.5 | 0.28 | Hydrate 5 |
| 20 | THF | 0.8 | 0.5 | 0.35 | Hydrate 5 + Hydrate 1 |

Pure Hydrate 5 was observed in a range of 0.1-0.3 of water activity. Above this threshold, Hydrate 1 started appearing. Based on these results ($a_w$>0.35), it is possible to estimate the minimum ratio of water required to achieve the formation of Hydrate 1 in other solvents such as IPA (>2.5%), acetone (>1.8%) or ethanol (>4.3%).

Summary

Table 5 Summary of Forms shows the correspondence between each crystalline form and the name that was tentatively used during the study, and reported throughout the update meetings, together with a description of the nature of the crystalline form.

TABLE 5

Summary of Forms

| Name | Description |
|---|---|
| Hydrate 1 | Stable tri-hydrate |
| Hydrate 2 | Metastable, hexa-hydrate |
| Hydrate 3 | Metastable, suspected mono-hydrate |
| Hydrate 4 | Metastable, suspected hemi-hydrate (maybe lower stoichiometry) |
| Hydrate 5 | Metastable, di-hydrate |
| Hydrate 6 | Metastable, suspected mono-hydrate, only isolated as a mixture with Hydrate 5 |
| Hydrate 7 | Metastable, only isolated as a mixture with Hydrate 1, undefined |

Figure 6:
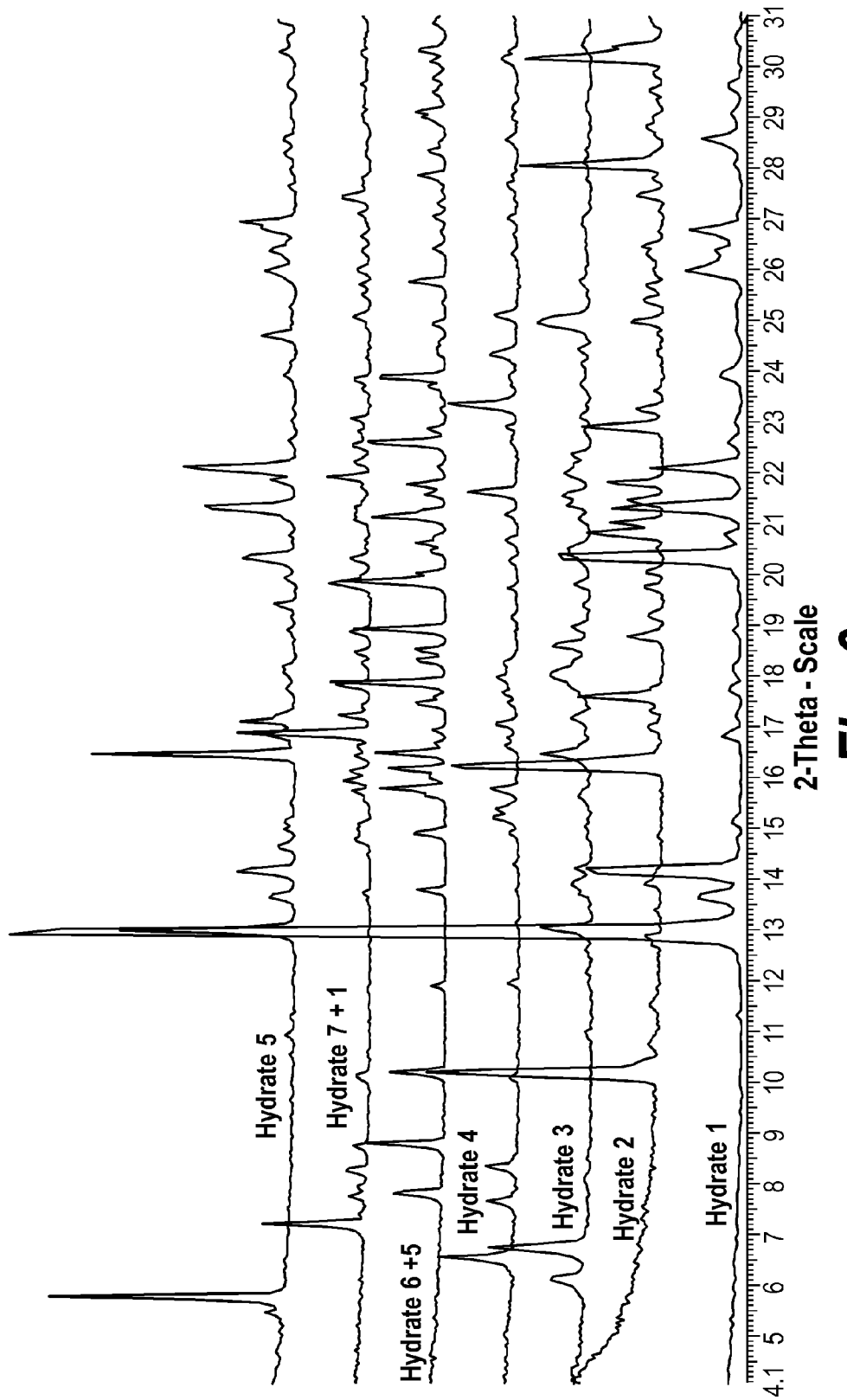
FIG. 6 depicts the X-ray powder diffraction patterns of a number of hydrate forms of sodium (2S,5R)-2-(1,3,4-oxadiazol-2-yl)-7-oxo-1,6-diazabicyclo[3.2.1]octan-6-yl sulfate identified in the polymorph studies described herein.

FIG. 6 shows XRPD spectra of the various polymorph forms of sodium (2S,5R)-2-(1,3,4-oxadiazol-2-yl)-7-oxo-1,6-diazabicyclo[3.2.1]octan-6-yl sulfate.

Hydrate 1 is the most stable crystalline form of sodium (2S,5R)-2-(1,3,4-oxadiazol-2-yl)-7-oxo-1,6-diazabicyclo[3.2.1]octan-6-yl sulfate at ambient conditions (25° C. and 40% RH) (see FIG. 2) compared to the other hydrates described herein.

Figure 7:
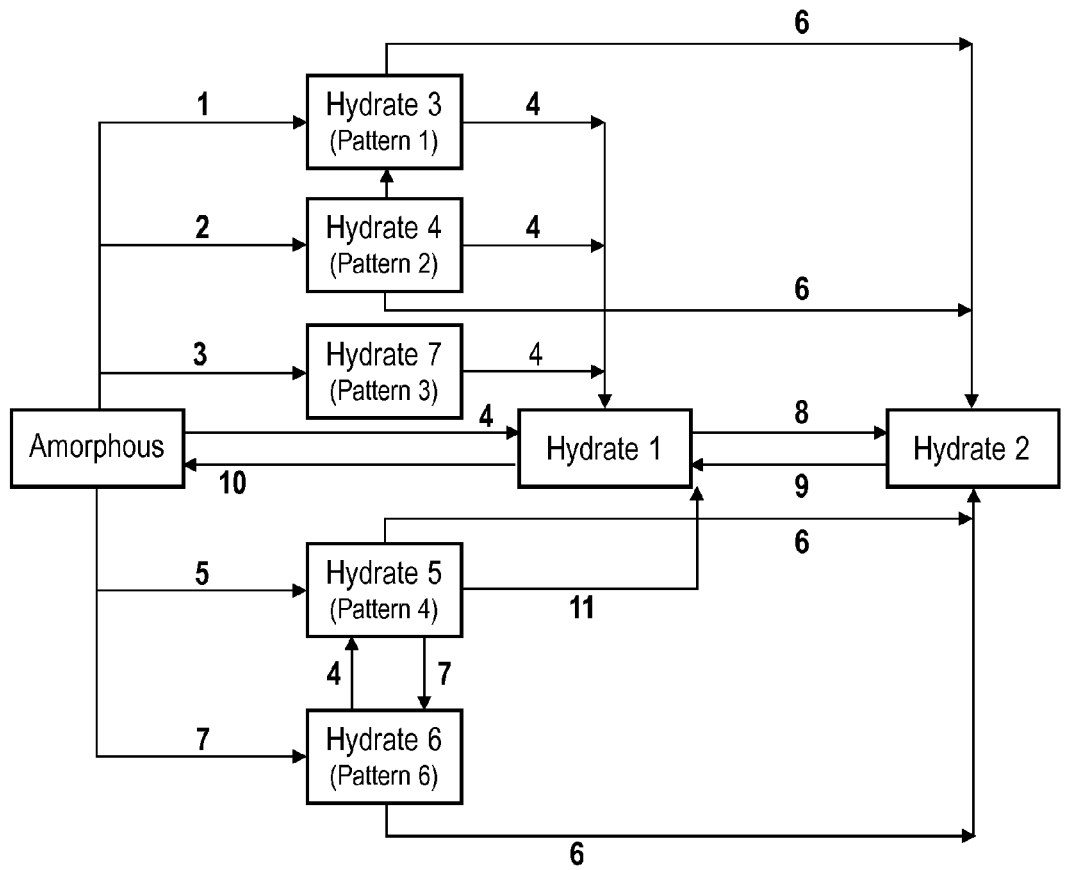
FIG. 7 shows a diagram that summarizes the relative thermodynamic relationships between the different hydrated forms of sodium (2S,5R)-2-(1,3,4-oxadiazol-2-yl)-7-oxo-1,6-diazabicyclo[3.2.1]octan-6-yl sulfate.

The diagram on FIG. 7 summarizes the relative thermodynamic relationships between the different hydrated forms of sodium (2S,5R)-2-(1,3,4-oxadiazol-2-yl)-7-oxo-1,6-diazabicyclo[3.2.1]octan-6-yl sulfate.

TABLE 6

XRPD Scanning Data of Hydrate 1 (FIG. 1)

| 2-Theta Angle | Intensity % |
|---|---|
| 11.38 | 1.2 |
| 13.09 | 100.0 |
| 13.79 | 6.4 |
| 14.29 | 21.6 |
| 15.29 | 1.9 |
| 16.99 | 3.2 |
| 17.39 | 1.3 |
| 17.89 | 2.2 |
| 18.29 | 1.7 |
| 18.94 | 1.7 |
| 20.49 | 25.4 |
| 21.46 | 18.1 |
| 22.21 | 12.9 |
| 22.73 | 2.4 |
| 23.19 | 1.5 |
| 24.09 | 3.5 |
| 24.94 | 1.3 |
| 25.41 | 1.3 |
| 26.10 | 8.1 |
| 26.87 | 7.6 |
| 28.20 | 1.6 |
| 28.65 | 5.9 |
| 29.17 | 2.0 |
| 29.78 | 2.3 |
| 30.21 | 1.0 |
| 30.67 | 1.4 |
| 31.98 | 1.8 |
| 33.46 | 6.2 |
| 33.97 | 3.5 |
| 35.30 | 1.7 |
| 35.87 | 1.6 |
| 37.34 | 1.7 |
| 40.28 | 2.1 |
| 41.77 | 1.6 |

XRPD Scanning Data of Hydrates 2, 3, 4, and 5 (FIG. 6)

TABLE 7

Hydrate 2

| Angle 2-Theta ° | Intensity Count % |
|---|---|
| 10.16 | 100.0 |
| 10.75 | 9.5 |
| 11.51 | 8.6 |
| 12.85 | 10.7 |
| 13.37 | 6.9 |
| 13.89 | 11.0 |
| 16.23 | 89.7 |
| 17.00 | 9.3 |
| 17.62 | 38.0 |
| 18.79 | 17.7 |
| 19.23 | 9.4 |
| 19.78 | 10.7 |
| 20.04 | 10.1 |
| 20.53 | 6.1 |
| 20.80 | 34.3 |
| 21.08 | 25.0 |
| 21.43 | 17.8 |
| 21.79 | 26.0 |
| 22.91 | 36.5 |
| 23.26 | 14.2 |
| 23.65 | 6.9 |
| 24.39 | 5.9 |
| 25.02 | 16.3 |
| 25.39 | 11.2 |
| 25.73 | 10.1 |
| 26.00 | 7.4 |
| 26.47 | 11.9 |
| 27.22 | 5.1 |
| 27.51 | 14.0 |
| 27.82 | 7.7 |
| 28.11 | 61.7 |
| 28.86 | 10.1 |
| 29.52 | 8.7 |
| 29.92 | 7.3 |
| 30.18 | 59.5 |
| 31.02 | 9.2 |
| 31.62 | 22.2 |

TABLE 7-continued

| Hydrate 2 | |
|---|---|
| Angle 2-Theta ° | Intensity Count % |
| 32.22 | 18.9 |
| 33.04 | 18.4 |
| 33.45 | 24.3 |

TABLE 8

| Hydrate 3 | |
|---|---|
| Angle 2-Theta ° | Intensity Counts % |
| 4.30 | 23.6 |
| 6.13 | 42.5 |
| 6.72 | 100.0 |
| 8.07 | 11.4 |
| 12.64 | 10.9 |
| 12.98 | 52.0 |
| 13.95 | 23.6 |
| 14.19 | 20.5 |
| 15.05 | 11.1 |
| 15.67 | 17.2 |
| 16.48 | 51.8 |
| 17.19 | 24.1 |
| 18.03 | 42.9 |
| 18.66 | 40.6 |
| 18.95 | 23.2 |
| 19.36 | 12.2 |
| 19.82 | 20.9 |
| 20.46 | 26.8 |
| 21.12 | 16.7 |
| 21.43 | 27.7 |
| 21.62 | 31.9 |
| 22.01 | 30.0 |
| 22.39 | 23.2 |
| 22.85 | 11.7 |
| 23.17 | 15.4 |
| 23.78 | 15.0 |
| 24.20 | 14.0 |
| 24.43 | 17.3 |
| 24.99 | 54.8 |
| 25.76 | 15.7 |
| 26.95 | 14.1 |
| 27.85 | 10.1 |
| 28.18 | 12.2 |
| 29.25 | 10.1 |
| 30.48 | 14.0 |

TABLE 9

| Hydrate 4 | |
|---|---|
| Angle 2-Theta ° | Intensity Count % |
| 6.54 | 100.0 |
| 7.64 | 43.9 |
| 8.34 | 44.4 |
| 10.08 | 17.2 |
| 11.95 | 17.0 |
| 13.14 | 9.6 |
| 14.30 | 12.1 |
| 14.91 | 18.2 |
| 15.21 | 37.4 |
| 15.39 | 33.8 |
| 15.80 | 36.7 |
| 16.63 | 22.7 |
| 17.08 | 30.2 |
| 17.67 | 22.9 |
| 17.97 | 32.8 |
| 18.26 | 24.2 |

TABLE 9-continued

| Hydrate 4 | |
|---|---|
| Angle 2-Theta ° | Intensity Count % |
| 19.16 | 14.1 |
| 19.74 | 17.3 |
| 20.27 | 15.1 |
| 20.69 | 21.7 |
| 21.19 | 21.7 |
| 21.63 | 62.4 |
| 22.65 | 13.7 |
| 22.94 | 19.1 |
| 23.38 | 85.0 |
| 23.89 | 15.3 |
| 24.36 | 39.9 |
| 25.12 | 32.8 |
| 26.34 | 12.8 |
| 27.04 | 17.1 |
| 27.69 | 17.4 |
| 28.60 | 19.2 |
| 29.21 | 11.5 |
| 30.16 | 23.8 |
| 33.68 | 13.4 |

TABLE 10

| Hydrate 5 | |
|---|---|
| Angle 2-Theta ° | Intensity Count % |
| 7.81 | 46.3 |
| 8.80 | 71.5 |
| 10.20 | 52.0 |
| 11.88 | 14.4 |
| 13.79 | 27.9 |
| 14.94 | 28.6 |
| 15.76 | 58.0 |
| 16.18 | 50.3 |
| 16.50 | 62.4 |
| 16.94 | 13.1 |
| 17.47 | 27.2 |
| 17.88 | 100.0 |
| 18.35 | 26.3 |
| 18.53 | 27.5 |
| 18.92 | 80.0 |
| 19.89 | 89.9 |
| 20.44 | 14.3 |
| 20.65 | 27.3 |
| 21.14 | 64.6 |
| 21.60 | 19.5 |
| 21.79 | 34.6 |
| 22.14 | 8.7 |
| 22.64 | 68.0 |
| 22.89 | 17.4 |
| 23.28 | 6.7 |
| 23.94 | 57.9 |
| 24.40 | 8.6 |
| 24.97 | 12.9 |
| 25.32 | 4.5 |
| 25.79 | 33.0 |
| 26.45 | 12.6 |
| 27.07 | 12.8 |
| 27.32 | 8.3 |
| 27.86 | 25.4 |
| 28.38 | 16.8 |
| 29.13 | 26.8 |
| 29.53 | 12.5 |
| 29.79 | 12.7 |
| 30.12 | 14.9 |
| 30.39 | 24.3 |
| 30.90 | 12.6 |
| 31.28 | 12.3 |
| 32.38 | 21.1 |
| 32.70 | 12.6 |
| 33.08 | 5.8 |

TABLE 10-continued

Hydrate 5

| Angle 2-Theta ° | Intensity Count % |
|---|---|
| 33.78 | 9.3 |
| 34.04 | 11.1 |
| 34.35 | 28.3 |
| 35.04 | 15.0 |
| 35.36 | 7.1 |
| 35.63 | 9.8 |
| 36.21 | 19.8 |
| 36.96 | 6.7 |
| 37.34 | 11.7 |
| 37.83 | 4.8 |
| 38.44 | 8.2 |
| 38.95 | 5.8 |
| 39.39 | 5.5 |
| 39.72 | 6.9 |
| 40.83 | 12.5 |

Example 4

Standard BLI Potentiation MIC Assay

The ability of compounds to potentiate the activity of β-lactams was demonstrated by determining the minimum inhibitory concentrations (MIC) of β-lactam and BLI compound combinations against various β-lactamase producing bacterial strains using the broth microdilution method. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition").

To prepare for MIC testing, frozen glycerol stocks of clinical isolates (*Klebsiella pneumoniae*, *Eschericia coli*, *Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 µg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with 25 µg/mL tetracycline) in 14 mL culture tubes. All strains were incubated at 37° C. with aeration (200 rpm) for ~2 hrs until the optical density at 600 nm ($OD_{600}$) was ≥0.1.

The two compound components of the assay were each diluted in CAMHB and added to the 96-well broth microdilution assay plates. 50 µL of the β-lactam was added to each well of the assay plate in 2-fold dilutions with final concentrations ranging from 128 to 0.13 µg/mL. 25 µL of the BLI compound was added to all wells in the broth microdilution plates at a final concentration of 4 µg/mL. Inoculum cultures were prepared by standardizing the primary cultures to OD600=0.1 and then adding 20 µL of the adjusted primary culture per 1 mL CAMHB for clinical strains or CAMHB (supplemented with tetracycline at 100 µg/mL) for engineered strains, so that the final inoculum density was ~$10^5$ colony forming units per milliliter. Diluted inoculum cultures were used to inoculate 25 µL per well in 96-well broth microdilution assay plates. The final volume of each well was 100 µL and contained a β-lactam at different concentrations, a BLI compound at 4 µg/mL concentration, the bacterial culture at an OD600 of approximately 0.001 and when necessary tetracycline at 25 µg/mL.

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. MIC values were defined as the lowest concentration producing no visible turbidity.

MIC values of –Hydrate 1 are shown in Table A.

Example 5

Synergy MIC (sMIC) Assay

The synergy MIC (sMIC) assay determines the concentration of the BLI required to potentiate the activity of a fixed concentration of a β-lactam antibiotic against β-lactamase producing bacterial strains. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition"). The assay is set-up by serially diluting the BLI across 11 of the 12 wells in each row of a 96-well broth microdilution assay plate, adding the β-lactam at a fixed concentration to all wells in the assay plate, inoculating the assay plate with bacterial strains, and determining the lowest concentration of BLI required to inhibit overnight bacterial growth. Bacterial growth in the $12^{th}$ well of the assay plate, which contains the β-lactam at a fixed concentration but does not contain any BLI, demonstrates that the bacterial strains are resistant to the β-lactam antibiotic (e.g. ceftolozane) at the fixed concentration of 4 µg/mL.

To prepare for MIC testing, frozen glycerol stocks of clinical isolates (*Klebsiella pneumoniae*, *Eschericia coli*, *Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 µg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with tetracycline at 25 µg/mL) in 14 mL culture tubes. All strains were incubated at 37° C. with aeration (200 rpm) for ~2 hrs until the OD600 was ≥0.1.

The two compound components of the assay were each prepared in CAMHB and added to the 96-well broth microdilution assay plates. 50 µL of the BLI was added to each well of the assay plate in 2-fold dilutions with final concentrations ranging from 128 to 0.13 µg/mL. 25 µL of the β-lactam was added to all wells in the broth microdilution plates at a final concentration of 4 µg/mL. Inoculum cultures were prepared by standardizing the primary cultures to OD600=0.1 and then adding 20 µL of the adjusted primary culture per 1 mL CAMHB for clinical strains or CAMHB (supplemented with tetracycline at 100 µg/mL) for isogenic strains, so that the final inoculum density was ~$10^5$ colony forming units per milliliter. Diluted inoculum cultures were used to inoculate 25 µL per well in 96-well broth microdilution assay plates. The final volume of each well was 100 µL and contained a BLI at different concentrations, a β-lactam at 4 µg/mL concentration, the bacterial culture at an OD600 of approximately 0.001 and when necessary tetracycline at 25 ug/mL.

Interpreting the sMIC Data:

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. sMIC values were defined as the lowest concentration producing no visible turbidity.

The sMIC values represent the amount of BLI required to potentiate the activity of 4 µg/ml of CXA-101 (Ceftolozane) or ceftazidime to inhibit the growth of the β-lactamase producing bacteria.

sMIC values of Hydrate 1 are shown in Table B.

Example 6

Inhibition Kinetics

Inhibition or inactivation of KPC-2 by test inhibitors was assessed using 100 µM nitrocefin (NCF) as a reporter substrate. Assays were performed in 1×PBS pH 7.4, 0.1 mg/ml BSA, in 96-well half area plates, 50 µl reaction volume. NCF was dissolved in DMSO and diluted in assay buffer. Test inhibitors were dissolved in water or DMSO and serially diluted in the assay with final concentrations between 2000-0.195 µM.

The enzyme activity in the presence of varying concentrations of test inhibitor was determined by monitoring the hydrolysis of NCF spectrophotometrically at 486 nm, for 5 minutes, 25° C., using a SpectraMax Plus384 microplate reader with SoftMax Pro software (Molecular Devices). Data analysis was performed using GraphPad Prism (GraphPad Software, Inc.).

Progress curves were fit to a first-order rate decay equation (Eq. 1) to determine $k_{observed}$ ($k_{obs}$).

$k_{obs}$ vs. inhibitor concentration [I] curves were then fit to Eq.2 to determine the inhibitor dissociation constant (K) and the first order rate constant of enzyme inactivation at infinite inhibitor concentration ($k_{inact}$). Kinetics results from the test of Hydrate 1 against the KPC-2 β-lactamase showed 134-163 mM$^{-1}$ s$^{-1}$ (Kinact/K mM$^{-1}$ s$^{-1}$).

$$Y_t = V_0 * (1 - e^{(-k_{obs}*t)})/k_{obs} \qquad \text{Eq. 1}$$

Where Y is the absorbance at time t, $V_0$ is the uninhibited enzyme velocity, $k_{obs}$ is the observed rate constant of the enzyme inactivation.

$$k_{obs} = k_{inact} * [I]/([I] + K(1 + S/K_m)) \qquad \text{Eq. 2}$$

Where S is the NCF concentration, $K_m$ is the KPC-2 $K_m$ for NCF.

TABLE A

Standard BLI Potentiation MIC Assay Against a Panel of Isogenic and Clinical Strains Expressing β-Lactamases

| Strain # | β-Lactamase | Bkgd | No BLI | Hydrate 1 |
|---|---|---|---|---|
| Eco.2806 | KPC-2 | isogenic | E | A |
| Pae.2808 | KPC-2 | clinical | E | C |
| Kpn.2478 | KPC-2, TEM+ | clinical | E | C |
| Kpn.2490 | KPC-3, SHV+, TEM+ | clinical | E | A |
| Kpn.2783 | CTX-M-15, SHV+, TEM+ | clinical | E | A |
| Kpn.571 | TEM-26 | clinical | D | A |
| Pae.2885 | AmpC | clinical | B | A |
| Cfr.568 | AmpC | clinical | E | B |
| Ecl.569 | AmpC | clinical | E | A |
| Kpn.2914 | KPC-2, SHV+ | clinical | D | B |
| Kpn.2913 | KPC-2, SHV+ | clinical | D | A |
| Kpn.2917 | KPC-2, SHV+ | clinical | D | A |
| Kpn.2918 | KPC-3, SHV+, TEM+ | clinical | E | B |
| Kpn.2909 | KPC-3, SHV+, TEM+ | clinical | E | B |
| Eco.2711 | KPC | clinical | D | A |
| Eco.2781 | KPC-2, TEM+ | clinical | C | A |
| Kpn.2926 | CTX-M-15, OXA-48 | clinical | E | B |
| Pae.2757 | AmpC over-expn | clinical | C | B |
| Pae.2863 | AmpC de-repress | clinical | C | B |
| Eco.2843 | DHA-1 | isogenic | E | A |
| Eco.2491 | CMY-2 | clinical | D | A |
| Eco.2902 | Aba-ADC-33 | isogenic | E | B |
| Eco.2840 | KPC-4 | isogenic | E | B |
| Eco.2845 | OXA-15 | isogenic | E | B |
| MIC90 | | | E | B |
| MIC50 | | | E | B |

A = 0.25-0.5 µg/mL; B = 1-2 µg/mL; C = 4-8 µg/mL; D = 16-32 µg/mL; E > 64 µg/mL

TABLE B

Synergy MIC (sMIC) Against a Panel of Isogenic and Clinical Strains Expressing β-lactamases

| β-Lactamase | Bkgd | Sp | β-Lactam (4 µg/mL) | Hydrate 1 |
|---|---|---|---|---|
| none | isogenic | Eco | none | F |
| KPC-2 | isogenic | Eco | CXA-101 | AA |
| OXA-15 | isogenic | Eco | CXA-101 | B |
| CTX-M-15 | isogenic | Eco | CXA-101 | A |
| SHV-12 | isogenic | Eco | CXA-101 | B |
| P99 | isogenic | Eco | CXA-101 | AA |
| KPC-2 | clinical | Kpn | CXA-101 | C |
| KPC-2 | clinical | Pae | CXA-101 | C |

AA = <0.25 µg/mL; A = 0.25-0.5 µg/mL; B = 1-2 µg/mL; C = 4-8 µg/mL; D = 16-32 µg/mL; E = 64 µg/mL; F = ≥128 µg/mL

What is claimed is:

1. Hydrate 1 of sodium (2S,5R)-2-(1,3,4-oxadiazol-2-yl)-7-oxo-1,6-diazabicyclo[3.2.1]octan-6-yl sulfate, wherein Hydrate 1 is characterized by an X-ray powder diffraction pattern having peaks expressed in degrees-2-theta at angles 13.1±0.2°, 14.3±0.2°, 20.5±0.2°, and 21.5±0.2°.

2. The hydrate 1 of claim 1, wherein the X-ray powder diffraction pattern further comprises a peak expressed in degrees-2-theta at angles 22.2±0.2°.

3. The hydrate 1 of claim 2, wherein the X-ray powder diffraction pattern further comprises peaks expressed in degrees-2-theta at angles 13.8±0.2°, 26.1±0.2°, 26.9±0.2°, 28.7±0.2°, and 33.5±0.2°.

4. The hydrate 1 of claim 3, wherein the X-ray powder diffraction pattern comprises peaks expressed in degrees-2-theta at angles 13.1±0.2°, 13.8±0.2°, 20.5±0.2°, 14.3±0.2°, 21.5±0.2°, 22.2±0.2°, 26.1±0.2°, 26.9±0.2°, 33.5±0.2°, and 28.7±0.2°.

5. A pharmaceutical composition comprising the Hydrate 1 of sodium (2S,5R)-2-(1,3,4-oxadiazol-2-yl)-7-oxo-1,6-diazabicyclo[3.2.1]octan-6-yl sulfate, and a pharmaceutically acceptable carrier, wherein Hydrate 1 is characterized by an X-ray powder diffraction pattern having peaks expressed in degrees-2-theta at angles 13.1±0.2°, 14.3±0.2°, 20.5±0.2°, and 21.5±0.2°.

6. The pharmaceutical composition of claim 5, wherein the X-ray powder diffraction pattern further comprises a peak expressed in degrees-2-theta at angle 22.2±0.2°.

7. The pharmaceutical composition of claim 6, wherein the X-ray powder diffraction pattern further comprises peaks expressed in degrees-2-theta at angles 13.8±0.2°, 26.1±0.2°, 26.9±0.2°, 28.7±0.2°, and 33.5±0.2°.

8. A pharmaceutical composition comprising the Hydrate 1 of claim 1 and at least one β-lactam antibiotic, wherein Hydrate 1 is characterized by an X-ray powder diffraction pattern having peaks expressed in degrees-2-theta at angles 13.1±0.2°, 14.3±0.2°, 20.5±0.2°, and 21.5±0.2°.

9. The pharmaceutical composition of claim 8, wherein the X-ray powder diffraction pattern further comprises a peak expressed in degrees-2-theta at angle 22.2±0.2°.

10. The pharmaceutical composition of claim 9, wherein the X-ray powder diffraction pattern further comprises peaks expressed in degrees-2-theta at angles 13.8±0.2°, 26.1±0.2°, 26.9±0.2°, 28.7±0.2°, and 33.5±0.2°.

11. A method of treating a bacterial infection comprising administering to a subject in need thereof a therapeutically-effective amount of the compound of claim 1.

12. The method of claim 11, wherein the X-ray powder diffraction pattern further comprises a peak expressed in degrees-2-theta at angle 22.2±0.2°.

13. The method of claim 12, wherein the X-ray powder diffraction pattern further comprises peaks expressed in degrees-2-theta at angles 13.8±0.2°, 26.1±0.2°, 26.9±0.2°, 28.7±0.2°, and 33.5±0.2°.

14. A method of treating a bacterial infection comprising administering to a subject in need thereof a therapeutically-effective amount of the pharmaceutical composition of claim 5.

15. A method of treating a bacterial infection comprising administering to a subject in need thereof a therapeutically-effective amount of the pharmaceutical composition of claim 8.

16. A method of making the compound of claim 1 comprising:
    (a) combining sodium (2S,5R)-2-(1,3,4-oxadiazol-2-yl)-7-oxo-1,6-diazabicyclo[3.2.1]octan-6-yl sulfate and a solvent, such that a solution of sodium (2S,5R)-2-(1,3,4-oxadiazol-2-yl)-7-oxo-1,6-diazabicyclo[3.2.1]octan-6-yl sulfate is formed; and
    (b) combining an antisolvent with the solution, wherein the antisolvent is miscible with the solvent and wherein sodium (2S,5R)-2-(1,3,4-oxadiazol-2-yl)-7-oxo-1,6-diazabicyclo[3.2.1]octan-6-yl sulfate is partially or completely insoluble in the antisolvent, such that crystalline Hydrate 1 precipitates from the solution.

17. The method of claim 16, wherein the antisolvent in step (b) of the method is THF or acetonitrile.

18. A pharmaceutical composition comprising (2S,5R)-2-(1,3,4-oxadiazol-2-yl)-7-oxo-1,6-diazabicyclo[3.2.1]octan-6-yl sulfate obtained from a solution formed by dissolving a solid form of (2S,5R)-2-(1,3,4-oxadiazol-2-yl)-7-oxo-1,6-diazabicyclo[3.2.1]octan-6-yl sulfate characterized by an X-ray powder diffraction pattern having peaks expressed in degrees-2-theta at angles 13.1±0.2°, 14.3±0.2°, 20.5±0.2°, and 21.5±0.2°.

19. The pharmaceutical composition of claim 18, obtained by a process comprising the steps of:
    (a) forming a solution of a solid form of (2S,5R)-2-(1,3,4-oxadiazol-2-yl)-7-oxo-1,6-diazabicyclo[3.2.1]octan-6-yl sulfate characterized by an X-ray powder diffraction pattern having peaks expressed in degrees-2-theta at angles 13.1±0.2°, 14.3±0.2°, 20.5±0.2°, and 21.5±0.2°; and
    (b) obtaining the (2S,5R)-2-(1,3,4-oxadiazol-2-yl)-7-oxo-1,6-diazabicyclo[3.2.1]octan-6-yl sulfate in the pharmaceutical composition from the solution in step (a).

20. The pharmaceutical composition of claim 18, obtained by a process comprising the steps of:
    (a) dissolving a solid form of (2S,5R)-2-(1,3,4-oxadiazol-2-yl)-7-oxo-1,6-diazabicyclo[3.2.1]octan-6-yl sulfate characterized by an X-ray powder diffraction pattern having peaks expressed in degrees-2-theta at angles 13.1±0.2°, 14.3±0.2°, 20.5±0.2°, and 21.5±0.2° in an aqueous solution; and
    (b) lyophilizing the aqueous solution of step (a) to obtain the (2S,5R)-2-(1,3,4-oxadiazol-2-yl)-7-oxo-1,6-diazabicyclo[3.2.1]octan-6-yl sulfate in the pharmaceutical composition.

* * * * *